United States Patent
Somberg et al.

(10) Patent No.: US 12,258,309 B2
(45) Date of Patent: Mar. 25, 2025

(54) ULTRA SHORT ACTING ANTI-ARRHYTHMIC AGENTS

(71) Applicant: Academic Pharmaceuticals, INC., Lake Bluff, IL (US)

(72) Inventors: John Somberg, Lake Forest, IL (US); Robert J Chorvat, Chadds Ford, PA (US)

(73) Assignee: Academic Pharmcauticals, Inc., Lake Bluff, IL (US)

( * ) Notice: Subject to any disclaimer, the term of this patent is extended or adjusted under 35 U.S.C. 154(b) by 75 days.

(21) Appl. No.: 18/347,808

(22) Filed: Jul. 6, 2023

(65) Prior Publication Data

US 2024/0025846 A1    Jan. 25, 2024

Related U.S. Application Data

(63) Continuation of application No. 17/645,723, filed on Dec. 22, 2021, now Pat. No. 11,731,938.

(60) Provisional application No. 63/199,436, filed on Dec. 28, 2020.

(51) Int. Cl.
    *C07C 317/28*    (2006.01)

(52) U.S. Cl.
    CPC .................. *C07C 317/28* (2013.01)

(58) Field of Classification Search
    CPC ..................................... C07C 317/28
    See application file for complete search history.

(56) References Cited

U.S. PATENT DOCUMENTS

| | | | | |
|---|---|---|---|---|
| 10,793,519 | B2 * | 10/2020 | Somberg | C07C 311/00 |
| 11,286,235 | B2 * | 3/2022 | Somberg | C07C 311/08 |
| 11,731,938 | B2 * | 8/2023 | Somberg | C07C 317/28 |
| | | | | 514/256 |

OTHER PUBLICATIONS

Erhardt1, J. Med. Chem. 1983, 26, 1109-1112.*
Erhardt, J. Med. Chem. 1982, 25, 1402-1407.*
Tikosyn-Dofetilide Label, Revised Aug. 2019.
Erhardt, P.W., et al., Ultra-Short-Acting B-Adrenergic Receptor Blocking Agents. 1. (Aryloxy)propanolamines Containing Esters in the Nitrogen Substituent, J. Med. Chem. 1982, 25, 1402-1407.
Erhardt, P.W., et al., Ultra-Short-Acting B-Adrenergic Receptor Blocking Agents. 3. Ethylenediamine Derivatives of (Aryloxy)propanolamines Having Esters on the Aryl Function, J. Med. Chem. 1983, 26, 1109-1112.
Murray, K.T., et al., Suppression of ventricular arrhythmias in man by d-propanolol independent of beta-adrenergic receptor blockade, J. Clin. Invest. 1990, 83(3), 836-42.
Walker, D.K., et al., Significance of Metabolism in the Disposition and Action of the Antidysrhythmic Drug, Dofetilide, Drug Metab. Dispos. 1996, 24(4), 447-55.

* cited by examiner

*Primary Examiner* — Nizal S Chandrakumar
(74) *Attorney, Agent, or Firm* — Vance Intellectual Property

(57) ABSTRACT

Some aspects provide novel dofetilide derivatives and pharmaceutical compositions containing the same that are useful as pharmaceutical agents in the treatment of supraventricular and ventricular arrhythmias.

12 Claims, No Drawings

ULTRA SHORT ACTING ANTI-ARRHYTHMIC AGENTS

FIELD OF THE INVENTION

Herein are described novel dofetilide derivatives and pharmaceutical compositions containing the same. The derivatives and compositions are useful as pharmaceutical agents in the treatment of supraventricular and ventricular arrhythmias.

BACKGROUND OF THE INVENTION

There is a clinical need for a short acting effective anti-arrhythmic agent for the treatment of both supraventricular and ventricular arrhythmias in patients with arrhythmias. Two effective agents are amiodarone and dofetilide. Amiodarone has an exceedingly long half-life and a multitude of adverse toxicities. Dofetilide is also an effective anti-arrhythmic, but its use is limited by the worsening of arrhythmias at times, a problem termed proarrhythmia. While the half-life of dofetilide in man is shorter than amiodarone, the half-life of dofetilide is twelve hours on average, making the cessation of therapy if arrhythmias worsen, problematic. To dissipate, dofetilide takes a long time, which can be a major clinical problem.

The introduction of a short acting dofetilide-like drug would offer considerable advantage for the acute treatment of arrhythmias. Therefore, it is desirable to discover dofetilide-like compounds that metabolize faster than dofetilide.

SUMMARY OF THE INVENTION

Accordingly, in some aspects, there are described novel dofetilide derivatives stereoisomers or pharmaceutically acceptable salts thereof.

In some aspects, there are described novel pharmaceutical compositions, comprising: a pharmaceutically acceptable carrier and a therapeutically effective amount of at least one of the compounds described herein or a a stereoisomer or pharmaceutically acceptable salt thereof.

In some aspects, there are described novel methods of treating various therapeutic indications of dofetilide by administering to a subject a therapeutically effective amount of a compound described herein.

In some aspects, there are described compounds for use in medical therapy.

In some aspects, there is described the use of compounds described herein for the manufacture of a medicament for the treatment of supraventricular and ventricular arrhythmias.

These and other objects, which will become apparent during the following detailed description, have been achieved by the inventors' discovery that the presently claimed compounds or stereoisomers or pharmaceutically acceptable salt forms thereof are expected to be effective as dofetilide derivatives.

DETAILED DESCRIPTION OF THE INVENTION

All references cited herein are hereby incorporated in their entirety herein by reference.

Dofetilide is a sulfonamide class III antiarrhythmic agent and potassium channel blocker used in the treatment of atrial fibrillation and flutter. It can restore normal sinus rhythm (NSR) by selectively blocking cardiac ion channels of the rapid component of the delayed rectifier potassium current Ikr. This property prolongs cardiac action potential duration and effective refractory period due to delayed repolarization without affecting conduction velocity, resulting in NSR.

A short acting dofetilide derivative administered intravenously (IV) could be administered to patients in a supraventricular arrhythmia to affect termination. If the treating physician saw evidence of excessive QT prolongation, the IV dofetilide derivative could be stopped, avoiding adverse effects that could entail life threatening ventricular arrhythmias such as ventricular tachycardia or ventricular fibrillation.

In the pediatric population, the use of IV dofetilide has advantages over amiodarone, another anti-arrhythmic drug. Amiodarone has many adverse side effects, and its toxicity is especially problematic in pediatric patients. In addition, dofetilide is especially effective in some supraventricular arrhythmias that are unique to the pediatric patient. An arrhythmia post-operative, ectopic junctional tachycardia (JET) is especially susceptible to effective treatment employing dofetilide. Utilizing a short acting dofetilide derivative would terminate the arrhythmia and if toxicity develops from dofetilide derivative, the drug action could be rapidly stopped, providing an extra safety margin in the pediatric patient.

A rapidly metabolized dofetilide derivative could be used to slow atrial tachycardia, convert atrial tachycardia, slow the ventricular response to atrial fibrillation, or convert atrial fibrillation or atrial flutter. A rapid acting, short half-life drug would be especially effective in the post-operative coronary artery surgery patients. Oral dofetilide has been shown effective in preventing the high incidence of AF post-operative. An IV short acting agent would be useful in this situation affording pharmacologic benefit, while if excessive QT prolongation is noted, or ventricular arrhythmias develop, the agent could be stopped with rapid dissipation of the adverse pharmacologic actions. This agent would possess the efficacy advantages of dofetilide with a new safety margin, offering considerable therapeutic advantage.

A short acting dofetilide derivative administered IV could be used for loading in atrial fibrillation patients to target Cmax ss (steady state)(patient specific and likely dependent upon renal clearance). If the treating physician saw evidence of excessive QT prolongation and/or Torsade de Pointes develops, the IV dofetilide derivative could be stopped and the dofetilide derivative would very rapidly dissipate. This would greatly increase patient safety and reduce the risk of life threatening arrhythmias caused by dofetilide.

As a result, in some aspects, there is described a novel dofetilide derivative that is expected to be metabolized by human esterases faster than dofetilide (~8-10 hours for terminal elimination half-life of dofetilide). This novel anti-arrhythmic agent is expected to be rapidly metabolized to reduce the time of the desired activity of the administered agent and minimize the side effects due to prolonged exposure, which have been observed with dofetilide.

In some aspects, the rapid metabolization is achieved by introducing an ester into dofetilide to increase its metabolism by esterases and thereby reduce its half-life to be less than that of unmodified dofetilide.

In some aspects, there is described a novel compound selected from Formulae I-VI:

| Formula # | Formula |
|---|---|
| I | *(structure: YO$_2$SHN-phenyl-(CH$_2$)$_p$-CH(CO$_2$R)-N(R')-CH$_2$CH$_2$-O-phenyl-NHSO$_2$Y)* |
| II | *(structure: YO$_2$SHN-phenyl-(CH$_2$)$_p$-CH[C(O)NH-CH(Z)(CO$_2$R)]-N(R')-CH$_2$CH$_2$-O-phenyl-NHSO$_2$Y)* |
| III | *(structure: YO$_2$SHN-phenyl-(CH$_2$)$_n$-CH[C(O)NH-(CH$_2$)$_m$-CH(OH)-(CH$_2$)$_n$-CO$_2$R]-N(R')-CH$_2$CH$_2$-O-phenyl-NHSO$_2$Y)* |
| IV | *(structure: YO$_2$SHN-phenyl-CH$_2$CH$_2$-N(R')-CH$_2$CH$_2$-O-phenyl(CO$_2$R)(NHSO$_2$Y))* |
| V | *(structure: YO$_2$SHN-phenyl-CH$_2$CH$_2$-N(R')-CH$_2$CH$_2$-O-phenyl(NHSO$_2$Y)-C(O)NH-CH(Z)(CO$_2$R))* |
| VI | *(structure: YO$_2$SHN-phenyl-CH$_2$CH$_2$-N(R')-CH$_2$CH$_2$-O-phenyl(NHSO$_2$Y)-C(O)NH-(CH$_2$)$_m$-CH(OH)-(CH$_2$)$_n$-CO$_2$R)* | or a pharmaceutically acceptable salt thereof.

In some aspects, there are described novel compounds of Formula I or a stereoisomer or a pharmaceutically acceptable salt thereof:

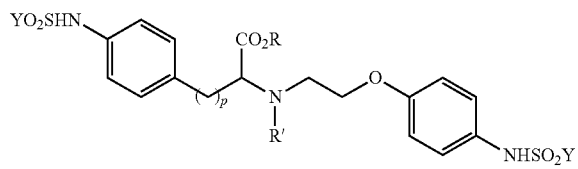

I wherein:
R is selected from H, $C_{1-6}$ alkyl, $C_{3-6}$ alkenyl, and $C_{3-6}$ alkynyl;
R' is selected from H, $C_{1-6}$ alkyl, $-CH_2C_6H_5$, and $-COCH_3$;
Y, at each occurrence, is independently selected from $CH_3$, $CH_2CH_3$, $CH_2CH_2CH_3$, and $CH(CH_3)_2$; and,
p is selected from 1 and 2.

In some aspects, there are described novel compounds of Formula I-A or a stereoisomer or a pharmaceutically acceptable salt thereof:

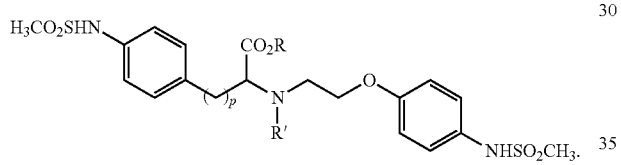

I-A

In some aspects, there are described novel compounds of Formula II or a stereoisomer or a pharmaceutically acceptable salt thereof:

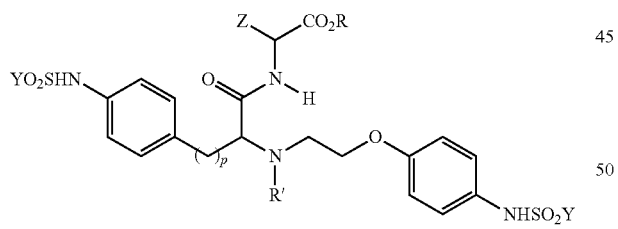

II wherein:
R is selected from H, $C_{1-6}$ alkyl, $C_{3-6}$ alkenyl, and $C_{3-6}$ alkynyl;
R' is selected from $C_{1-3}$ alkyl and $-COCH_3$;
Z is selected from H, $C_{1-6}$ alkyl, $CH_2OH$, $CH(CH_3)OH$, $C(CH_3)_2OH$, and $(CH_2)_n$-phenyl;
Y, at each occurrence, is independently selected from $CH_3$, $CH_2CH_3$, $CH_2CH_2CH_3$, and $CH(CH_3)_2$; and,
p is selected from 1 and 2.

In some aspects, there are described novel compounds of Formula II-A or a stereoisomer or a pharmaceutically acceptable salt thereof:

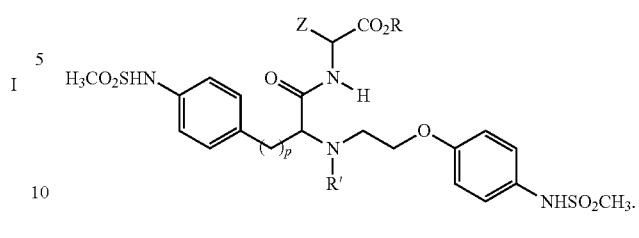

II-A

In some aspects, there are described novel compounds of Formula III or a stereoisomer or a pharmaceutically acceptable salt thereof:

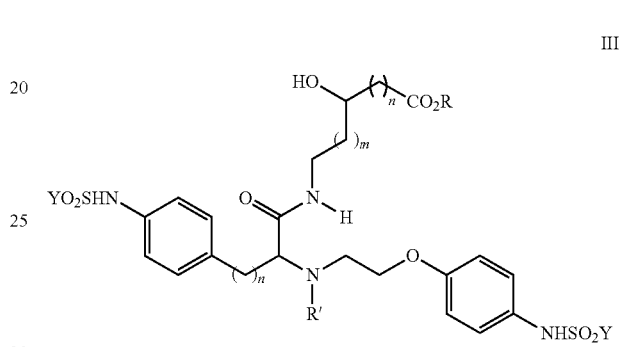

III wherein:
R is selected from H, $C_{1-6}$ alkyl, $C_{3-6}$ alkenyl, and $C_{3-6}$ alkynyl;
R' is selected from H, $C_{1-3}$ alkyl, and $-COCH_3$;
Y, at each occurrence, is independently selected from $CH_3$, $CH_2CH_3$, $CH_2CH_2CH_3$, and $CH(CH_3)_2$;
m is selected from 0 and 1; and, n, at each occurrence, is independently selected from 0 and 1.

In some aspects, there are described novel compounds of Formula III-A or a stereoisomer or a pharmaceutically acceptable salt thereof:

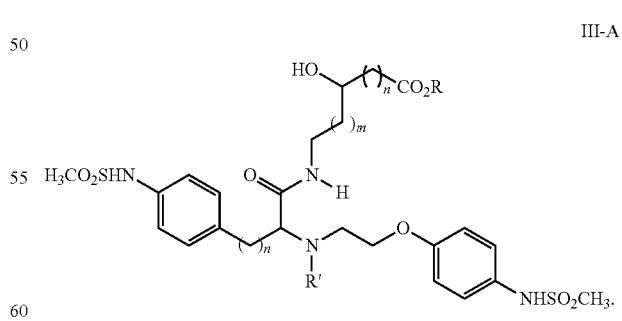

III-A

In some aspects, there are described novel compounds of Formula IV or a stereoisomer or a pharmaceutically acceptable salt thereof:

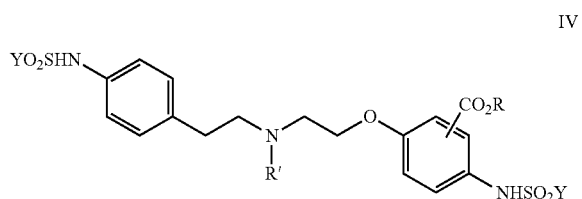

IV wherein:

R is selected from H, $C_{1-6}$ alkyl, $C_{3-6}$ alkenyl, and $C_{3-6}$ alkynyl;

R' is selected from H, $C_{1-3}$ alkyl, and —COCH$_3$; and,

Y, at each occurrence, is independently selected from CH$_3$, CH$_2$CH$_3$, CH$_2$CH$_2$CH$_3$, and CH(CH$_3$)$_2$.

In some aspects, there are described novel compounds of Formula IV-A or a stereoisomer or a pharmaceutically acceptable salt thereof:

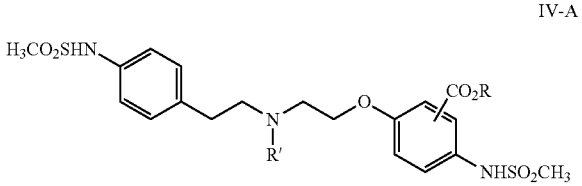

IV-A

In some aspects, there are described novel compounds of Formula IV-B or a stereoisomer or a pharmaceutically acceptable salt thereof:

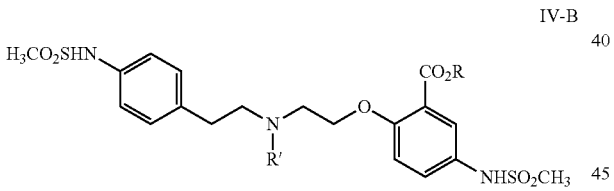

IV-B

In some aspects, there are described novel compounds of Formula IV-C or a stereoisomer or a pharmaceutically acceptable salt thereof:

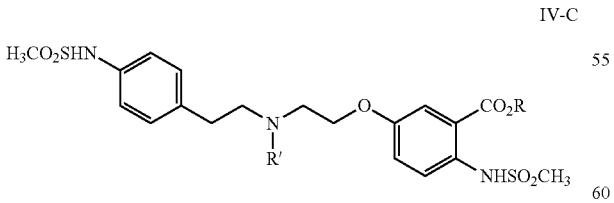

IV-C

In some aspects, there are described novel compounds of Formula V or a stereoisomer or a pharmaceutically acceptable salt thereof:

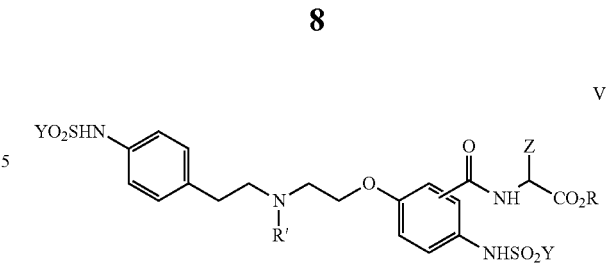

V wherein:

R is selected from H, $C_{1-6}$ alkyl, $C_{3-6}$ alkenyl, and $C_{3-6}$ alkynyl;

R' is selected from H, $C_{1-3}$ alkyl, and —COCH$_3$;

Z is selected from H, $C_{1-6}$ alkyl, CH$_2$OH, CH(CH$_3$)OH C(CH$_3$)$_2$OH, and (CH$_2$)$_n$-phenyl;

Y, at each occurrence, is independently selected from CH$_3$, CH$_2$CH$_3$, CH$_2$CH$_2$CH$_3$, and CH(CH$_3$)$_2$.

In some aspects, there are described novel compounds of Formula V-A or a stereoisomer or a pharmaceutically acceptable salt thereof:

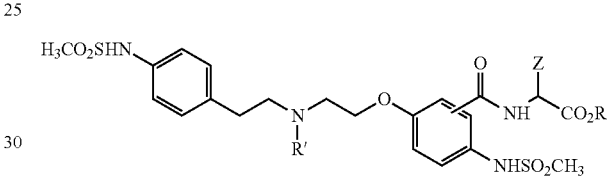

V-A

In some aspects, there are described novel compounds of Formula V-B or a stereoisomer or a pharmaceutically acceptable salt thereof:

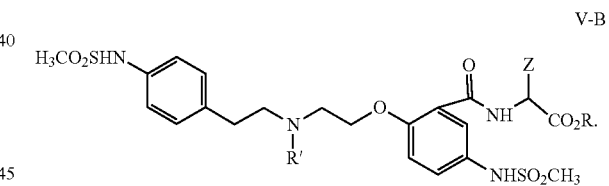

V-B

In some aspects, there are described novel compounds of Formula V-C or a stereoisomer or a pharmaceutically acceptable salt thereof:

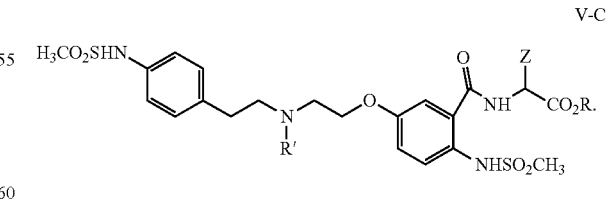

V-C

In some aspects, there are described novel compounds of Formula VI or a stereoisomer or a pharmaceutically acceptable salt thereof:

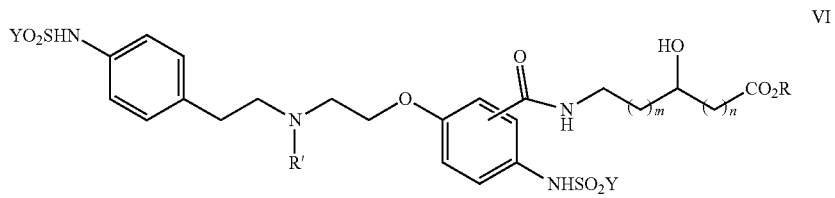

VI wherein:
R is selected from H, $C_{1-6}$ alkyl, $C_{3-6}$ alkenyl, and $C_{3-6}$ alkynyl;
R' is selected from $C_{1-3}$ alkyl;
Y, at each occurrence, is independently selected from $CH_3$, $CH_2CH_3$, $CH_2CH_2CH_3$, and $CH(CH_3)_2$;
m is selected from 0 and 1; and,
n is selected from 0 and 1.

In some aspects, there are described novel compounds of Formula VI-A or a stereoisomer or a pharmaceutically acceptable salt thereof:

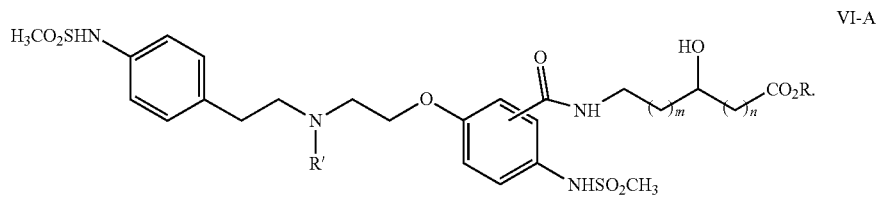

VI-A

In some aspects, there are described novel compounds of Formula VI-B or a stereoisomer or a pharmaceutically acceptable salt thereof:

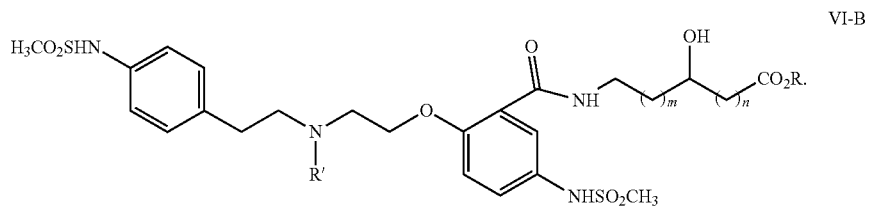

VI-B

In some aspects, there are described novel compounds of Formula VI-C or a stereoisomer or a pharmaceutically acceptable salt thereof:

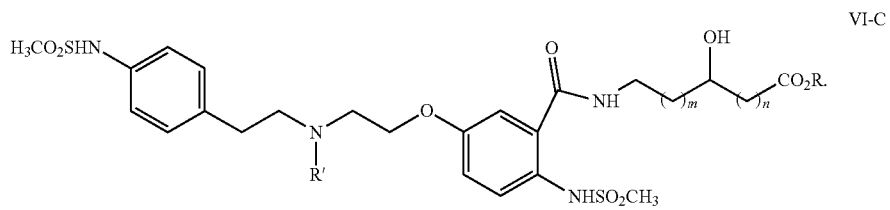

VI-C

In some aspects, there are described a novel compound of Formula I-VI-C, or a stereoisomer or pharmaceutically acceptable salt thereof, wherein: one or more hydrogens (H) are replaced by D. For example, R can be a D, a deuterated methyl group (e.g., CD₃) or the alkenyl or alkynyl hydrogens can be replaced by deuterium (e.g., —CD=CD-). In addition, wherever hydrogens are present in one of the Formulae or in one of the listed substituents (R, R', etc.), the hydrogens present (e.g., —CH₂—, alkyl, alkenyl, alkynyl, etc.) can be partially or fully replaced by D (e.g., —CD₂-, CD₃, etc.).

In some aspects, there are described novel compounds of Formula A or a stereoisomer or a pharmaceutically acceptable salt thereof:

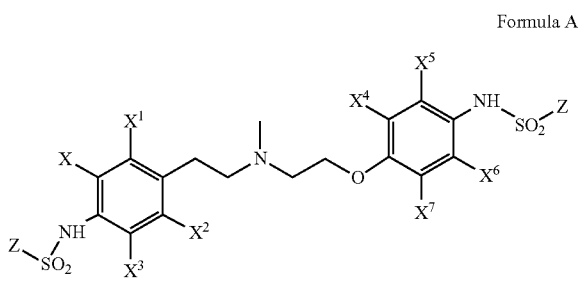

Formula A wherein:
- Z is, independently CH₃ or —(CH₂)ₘ—CO₂R, provided that at least one of Z is —(CH₂)ₘ—CO₂R;
- R is selected from H, C₁₋₆ alkyl, C₃₋₆ alkenyl, and C₃₋₆ alkynyl;
- m is selected from 0, 1, and 2; and,
- X-X⁷ are independently selected from H, —O—C₁₋₃ alkyl, C₁₋₃ alkyl, halogen, CF₃, nitro, and —CN.

In some aspects, there are described novel compounds of Formula A or a stereoisomer or a pharmaceutically acceptable salt thereof, wherein:
- Z is, independently CH₃ or —(CH₂)ₘ—CO₂R, provided that at least one of Z is —(CH₂)ₘ—CO₂R;
- R is C₁₋₆ alkyl;
- m is selected from 0 and 1; and,
- X-X⁷ are H.

In some aspects, there are described a novel compound of Formula 1 or a stereoisomer or a pharmaceutically acceptable salt thereof:

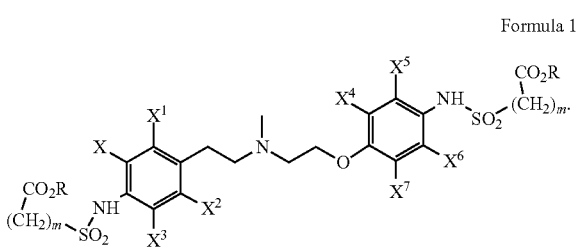

Formula 1

In some aspects, there are described a novel compound of Formula 1A or a stereoisomer or a pharmaceutically acceptable salt thereof:

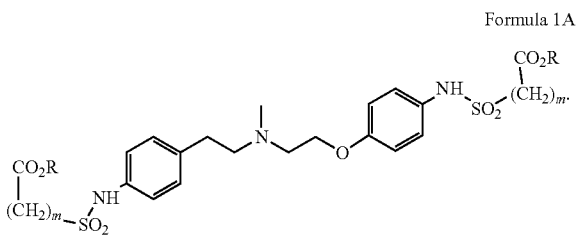

Formula 1A

In some aspects, there are described a novel compound of Formula 1B or a stereoisomer or a pharmaceutically acceptable salt thereof:

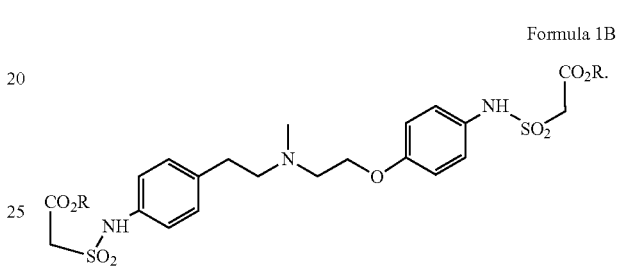

Formula 1B

In some aspects, there are described novel compounds of Formula 2 or a stereoisomer or a pharmaceutically acceptable salt thereof:

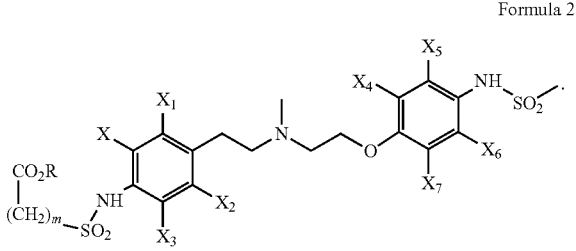

Formula 2

In some aspects, there are described a novel compound of Formula 2A or a stereoisomer or a pharmaceutically acceptable salt thereof:

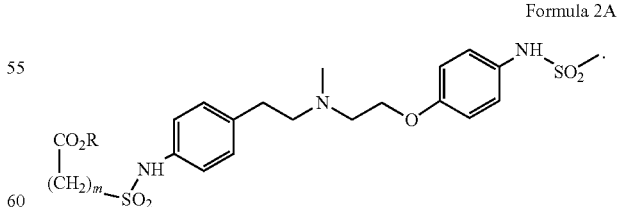

Formula 2A

In some aspects, there are described a novel compound of Formula 2B or a stereoisomer or a pharmaceutically acceptable salt thereof:

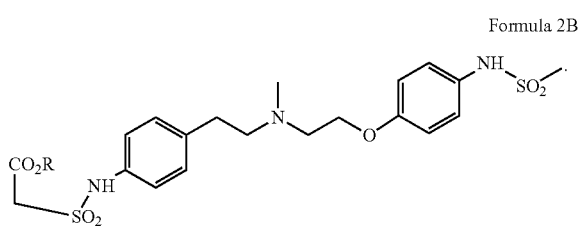

Formula 2B

In some aspects, there are described novel compounds of Formula 3 or a stereoisomer or a pharmaceutically acceptable salt thereof:

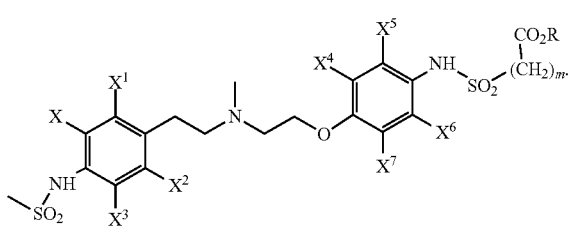

Formula 3

In some aspects, there are described a novel compound of Formula 3A or a stereoisomer or a pharmaceutically acceptable salt thereof:

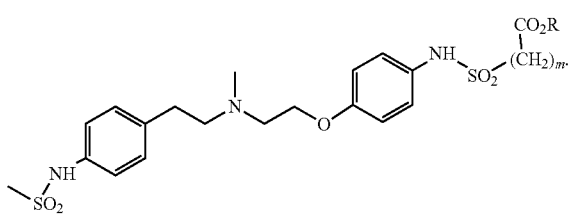

Formula 3A

In some aspects, there are described a novel compound of Formula 3B or a stereoisomer or a pharmaceutically acceptable salt thereof:

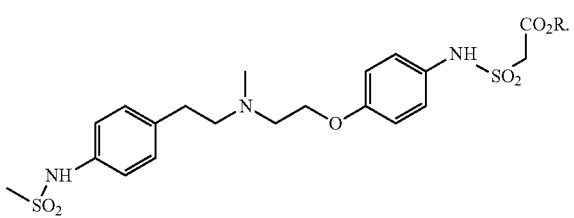

Formula 3B

In some aspects, there are described a novel compound of Formula A-3B, or a stereoisomer or pharmaceutically acceptable salt thereof, wherein: one or more hydrogens (H) are replaced by D. For example, R can be a D, a deuterated methyl group (e.g., $CD_3$) or the alkenyl or alkynyl hydrogens can be replaced by deuterium (e.g., —CD=CD-). In addition, wherever hydrogens are present in one of the Formulae or in one of the listed substituents (R, X, Z, etc.), the hydrogens present (e.g., —$CH_2$—, alkyl, alkenyl, alkynyl, etc.) can be partially or fully replaced by D (e.g., —$CD_2$-, $CD_3$, etc.).

In some aspects, there are described a novel pharmaceutical composition, comprising: a therapeutically effective amount of a compound described herein or a stereoisomer or a pharmaceutically acceptable salt thereof and a pharmaceutically acceptable carrier.

In some aspects, there are described a novel compound having a terminal elimination half-life less than 8 hours (recall that the terminal elimination half-life of dofetilide is ~8-10 hours). Additional examples include less than 7, 6, 5, 4, 3, 2, and 1 hour. Further examples include less than 60, 50, 40, 30, 20, and 10 minutes. Terminal elimination half-life is the time it takes for 50% of the compound to be metabolized and excreted (e.g., metabolized by CYP3A4 and excreted via the kidney).

With the compounds described herein being short acting, they offer the advantage of a superior therapeutic to toxic ratio. In another aspect, the pharmacologic action of the compounds described herein can be quickly terminated by stopping administration thereof to avoid adverse side effects. In another aspect, the compounds described herein can prolong cardiac repolarization and then prevent the recurrence of the arrhythmia if adequate drug concentration is maintained.

In some aspects, there are described a novel method of terminating or blocking the occurrence of an arrhythmia, comprising: administering to a patient in need thereof a therapeutically effective amount of a compound described herein or a stereoisomer or pharmaceutically acceptable salt thereof, wherein the arrhythmia is selected from: paroxysmal atrial tachycardia, junctional ectopic tachycardia, atrial flutter, atrial fibrillation, atrial tachycardia, junctional tachycardia, ventricular tachycardia, and ventricular fibrillation.

Blocking refers to preventing the recurrence of or reducting the frequency of recurrence of the indication for as long as the compound described herein is present in the patient at an effective concentration.

In some aspects, there are described a novel method of causing electrophysiological actions that are anti-arrhythmic, comprising: administering to a patient in need thereof a therapeutically effective amount of a compound described herein or a stereoisomer or pharmaceutically acceptable salt thereof, wherein the compound binds to the IKr and possibly IKs potassium channels, inhibiting them.

In some aspects, there are described a novel method of terminating a symptom selected from: paroxysmal atrial tachycardia, junctional ectopic tachycardia, atrial flutter, atrial fibrillation, atrial tachycardia, junctional tachycardia, ventricular tachycardia, and ventricular fibrillation, comprising: administering to a patient in need thereof a therapeutically effective amount of a compound described herein or a stereoisomer or pharmaceutically acceptable salt thereof.

In some aspects, there are described a novel method of blocking the development of or blocking a symptom selected from: atrial tachycardia, junctional ectopic tachycardia, atrial flutter, atrial fibrillation, junctional tachycardia, ventricular tachycardia, and ventricular fibrillation, comprising: administering to a patient in need thereof a therapeutically effective amount of a compound described herein or a stereoisomer or pharmaceutically acceptable salt thereof.

In another aspect, the patient had previously suffered from at least one of the symptoms and the therapy stops the reoccurrence of the symptom.

In some aspects, there are described a novel method of treating a symptom selected from: paroxysmal atrial tachycardia junctional ectopic tachycardia, atrial flutter, and atrial fibrillation that occurs peri or post-operatively in the pediatric or adult population, comprising: administering to a patient in need thereof a therapeutically effective amount of a compound described herein or a stereoisomer or pharmaceutically acceptable salt thereof.

In some aspects, there are described a novel method of treating electrical storm (repeated episodes of ventricular tachychardia (VT) or ventricular fibrillation (VF)), which can be due to myocardial infarction, cardiac arrest, and/or defibrillator implantation and/or testing, comprising: administering to a patient in need thereof a therapeutically effective amount of a compound described herein or a stereoisomer or pharmaceutically acceptable salt thereof.

In another aspect, route of administration is selected from: intravenous, oral, topical, sublingual, and bucal.

In some aspects, there are described a novel compound for use in therapy.

In some aspects, there are described the use of novel compounds for the manufacture of a medicament for the treatment of an indication recited herein.

In another aspect, examples of the molecular weight of the compounds described herein include (a) less than about 600, 650, 700, 750, 800, 850, 900, 950, or 1000 grams per mole; (b) less than about 950 grams per mole; (c) less than about 850 grams per mole; and, (d) less than about 750 grams per mole.

In another aspect, examples of the solubility of the compounds described herein include greater than 50 60, 70, 80, 90, 100, 110, 120, 130, 140, 150, 160, 170, 180, 190, 200, 210, 220, 230, 240, 250, 260, 270, 280, 290, 300, 400, 500, 600, 700, 800, 900 and 1000 ρg/mL.

Some aspects may be embodied in other specific forms without departing from the spirit or essential attributes thereof. This invention encompasses all combinations of aspects described herein. It is understood that any and all aspects described herein may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

DEFINITIONS

The examples provided in the definitions present in this application are non-inclusive unless otherwise stated. They include but are not limited to the recited examples.

A compound or compounds, as used herein, includes, where appropriate, stereoisomers and/or pharmaceutically acceptable salts thereof.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds described herein containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in some aspects. Specifically, cis and trans geometric isomers of the compounds described herein may also exist and may be isolated as a mixture of isomers or as separated isomeric forms. All processes used to prepare compounds described herein and intermediates made therein are part of some aspects. All tautomers of shown or described compounds are also considered to be part of some aspects.

Compounds with at least two stereocenters are referred to as being present in "diastereomeric excess" (de). The % de is determined by the following formula:

$$\% \text{ de} = (\% A - \% B)/(\% A + \% B)*100$$

wherein A=desired diastereomer, B=undesired diastereomer, and %=mole fraction. For example, 60% de refers to 80% of the desired diastereomer and 20% of the undesired diastereomer(s). Examples include 60, 70, 80, 90, 91, 92, 93, 94, 95, 96, 97, 98, to 99% de.

Some aspects includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term "substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

"Stable" means that the compound is suitable for pharmaceutical use.

Some aspects covers stable compounds and thus avoids, unless otherwise specified, the following bond types: heteroatom-halogen, N—S, O—S, O—O, and S—S.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

When an "ene" terminates a group it indicates the group is attached to two other groups. For example, methylene refers to a —$CH_2$-moiety.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ alkynyl includes $C_2$, $C_3$, $C_4$, $C_5$, and $C_6$ alkynyl groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups.

"Halo" or "halogen" refers to fluoro, chloro, bromo, and iodo.

"Counterion" is used to represent a small, negatively charged species, such as chloride, bromide, hydroxide, acetate, and sulfate.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting its development; and/or (c) relieving the disease-state, e.g., causing regression of the disease state until a desired endpoint is reached. Treating also includes the amelioration of a symptom of a disease, wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts described herein can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, PA, 1990, p 1445, the disclosure of which is hereby incorporated by reference.

"Therapeutically effective amount" includes an amount of a compound described herein that is effective when administered alone or in combination to an indication listed herein. "Therapeutically effective amount" also includes an amount of the combination of compounds claimed that is effective to treat the desired indication. The combination of compounds can be a synergistic combination. Synergy, as described, for example, by Chou and Talalay, Adv. Enzyme Regul. 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Formulations and Dosages

The compounds described herein can be formulated as pharmaceutical compositions and administered to a human patient in a variety of forms adapted to the chosen route of administration, e.g., orally, parenterally, by intravenous (e.g., continuously or bolus), intrathecal, intramuscular, topical, intradermal, intraperitoneal, intraocular, inhalation or subcutaneous routes. Exemplary pharmaceutical compositions are disclosed in "*Remington: The Science and Practice of Pharmacy*," A. Gennaro, ed., 20th edition, Lippincott, Williams & Wilkins, Philadelphia, PA.

Thus, the present compounds may be systemically administered, e.g., intravenously, in combination with a pharmaceutically acceptable carrier/excipient such as an inert diluent. The amount of active compound in such therapeutically useful compositions is such that an effective dosage level will be obtained.

The amount of the compound described herein or an active salt or derivative thereof, required for use in treatment will vary not only with the compound or salt selected but also with the route of administration, the nature of the condition being treated, and the age and condition of the patient, and will ultimately be at the discretion of the attendant physician or clinician. In general, however, a suitable dose will be in the range of about 100, 200, 300, 400, 500, 600, 700, 800, 900, to 1000 mg per dosage (e.g., twice per day (BID). Other examples include (a) about 200-800 mg per dosage and (b) about 400-600 mg dosage.

A compound described herein can also be given based on the weight of the patient. In general, a suitable weight-based dosage will be in the range of 3, 4, 5, 6, 7, 8, 9, to 10 mg/kg of body weight per dosage. Other examples include (a) about 4-9 mg/kg and (b) about 5-8 mg/kg of body weight per dosage.

The compounds described herein can be conveniently administered in unit dosage form, e.g., vials or pre-filled syringes, etc., containing (a) about 100-100 mg, (b) about 200-800 mg, and (c) about 400-600 mg of active ingredient per unit dosage form.

The compounds described herein can be administered to achieve peak plasma concentrations of the active compound of about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, to 3.5 ng/mL. These concentrations may be achieved, for example, by the intravenous injection (e.g., continuously or bolus) of a 0.005-0.5% solution of the active ingredient.

When a compound described herein is administered in combination with another agent or agents (e.g., co-administered), then the compound described herein and other agent can be administered simultaneously or in any order. They can be administered as a single pharmaceutical composition or as separate compositions. The administration of the compound described herein can be prior to the other agent(s), within minutes thereof, or up to hours (e.g., 24 or 48) or even days after the administration of the other agent(s). For example, the administration of the compound described herein can be within about 24 hours or within about 12 hours.

The compounds described herein may also be administered intravenously (e.g., continuously or bolus) or intraperitoneally by infusion or injection. Solutions of the compounds described herein or their salts can be prepared in water, optionally mixed with a nontoxic surfactant. For solubility purposes the compound(s) may also be solubilized in a lipid emulsion or administered in liposomes. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or using surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions. Sterilization can also be performed by rapid heating and cooling.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

The desired dose of the compounds described herein may conveniently be presented in a single dose or as divided doses administered at appropriate intervals, for example, as two, three, four or more sub-doses per day. The sub-dose itself may be further divided, e.g., into a number of discrete loosely spaced administrations.

Synthesis

The compounds described herein can be prepared in a number of ways known to one skilled in the art of organic synthesis (e.g., see U.S. Pat. No. 4,959,366. The compounds described herein can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one process scheme over another in order to obtain a desired compound. It will also be recognized that another major consideration in the planning of any synthetic route in this field is the judicious choice of the protecting group used for protection of the reactive functional groups present in the compounds described herein. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

One stereoisomer of a compound described herein may be more potent than its counterpart(s). Thus, stereoisomers are included in some aspects. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound described herein may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

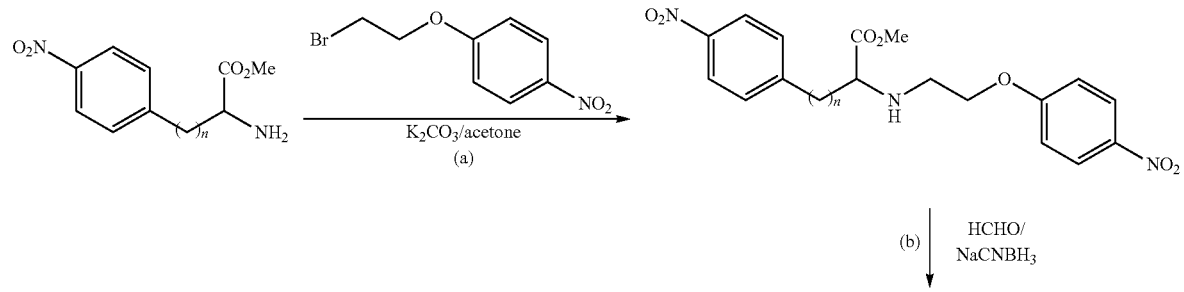

Scheme 1

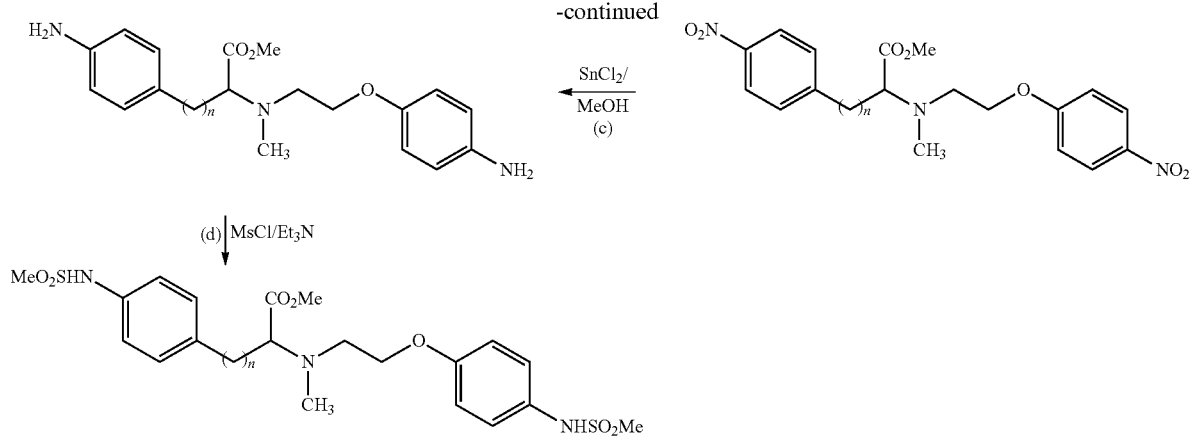

Scheme 1 shows the preparation of dofetiliide analogs and sodium cyano borohydride in methanol can produce the tertiary amine (step b). Reduction of the nitro groups using stannous chloride in methanol, or with Fe in methanol in the presence of hydrochloric acid, can produce the bis-anilino compound (step c). Further treatment of 4 with methanesulfonyl chloride in methylene chloride in the presence of triethylamine can afford the bis-sulfonamide (step d). To one skilled in the art, this route is amenable to variation to both the phenethylamine segment as well as the substituents on the central N-atom. with functionality to confer ultra-short activity to the molecules due to their propensity for rapid esterase hydrolysis to metabolites with greatly diminished, or absence of, parent compound activity. The approach to the synthesis of analogs of dofertilide and related compounds has been duly demonstrated (J Med Chem 45, 2953 (2002)). Treatment of N-methyl-4-nitrophenylalanine methyl ester with 2-(4-nitrophenoxy)-1-bromo ethane in the presence of potassium carbonate in acetonitrile can provide the secondary amine (step a). Alkylation of this amino compound using formalin

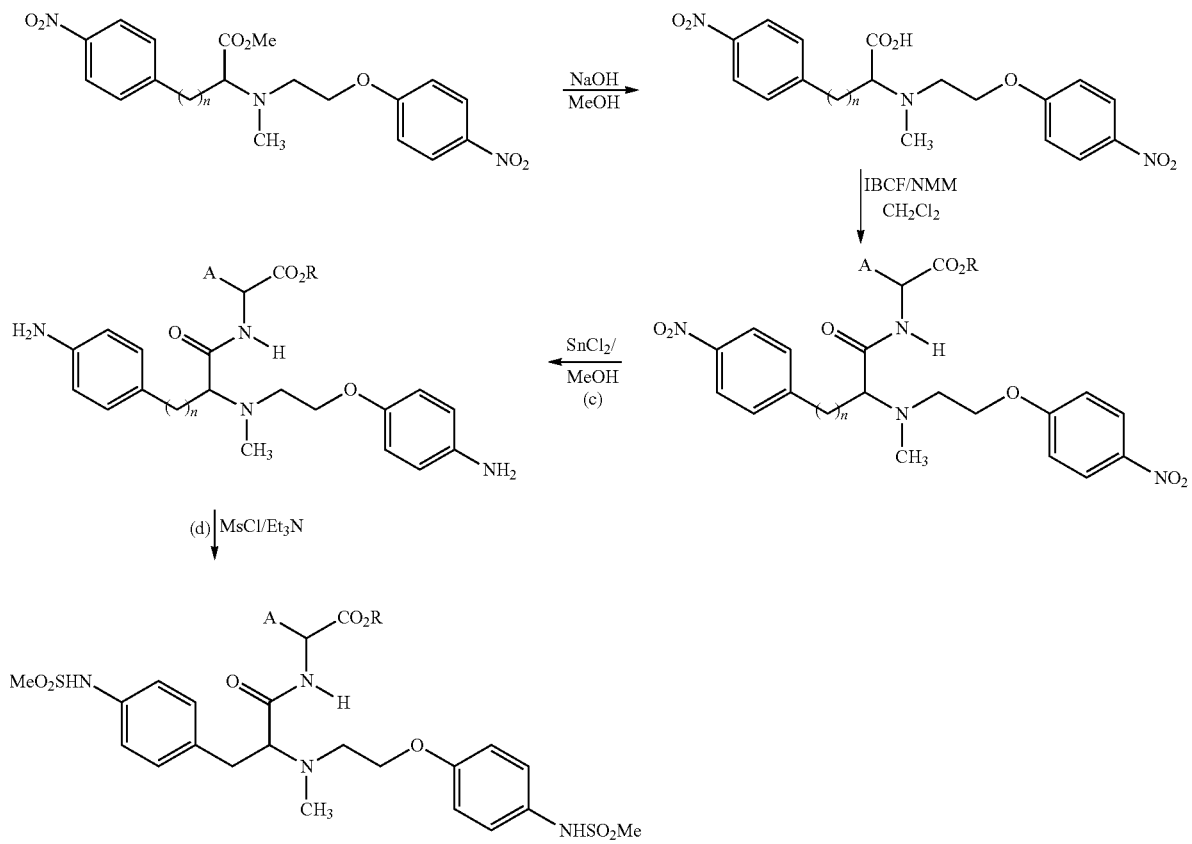

Scheme 2 shows the preparation of additional adducts of the ester of Scheme 1. The intermediate ester formed in step b of Scheme 1 can be hydrolyzed to the carboxylic acid (step a), and then coupled with various amino acid esters using isobutyl chloroformate in methylene chloride in the presence of n-methylmorpholine to afford the di-nitro esters (step b). Reduction of the nitro groups using anhydrous stannous chloride in methanol can yield the di-anilino esters (step c) and subsequent sulfonylation with mesyl chloride in the presence of triethyl amine can provide the bi-sulfonamides (step d).

Scheme 3

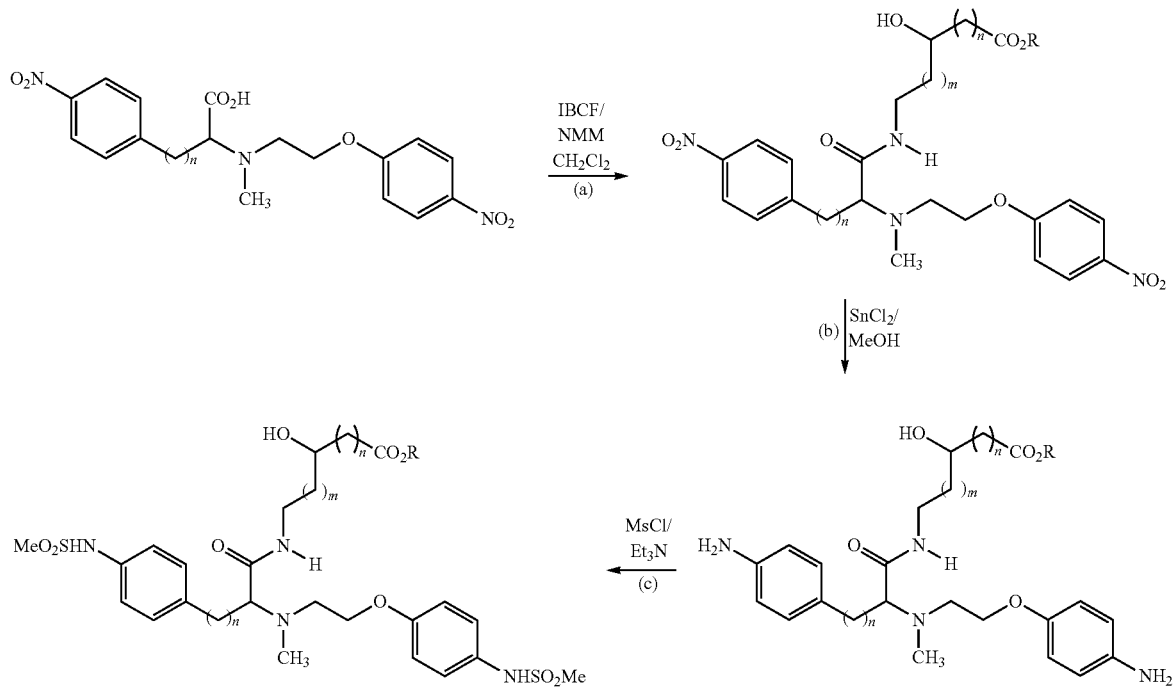

Scheme 3 shows the preparation of adducts of the side-chain ester of Scheme 2 with various straight-chain hydroxy amino esters (H$_2$N—CH$_2$—(CH$_2$)$_m$—CH(OH)—(CH$_2$)$_n$—CO$_2$R). The di-nitro carboxylic acid of Scheme 2 can be coupled with hydroxy butyric acid esters with IBCF (isobutyl chloroformate) in methylene chloride in the presence of NMM (N-methyl morpholine) to afford the hydroxyl ester adducts (step a). Reduction of the nitro groups with anhydrous stannous chloride in methanol can produce the di-anilino compound (step b). Subsequent treatment with mesyly chloride in methylene chloride in the presence of triethyl amine can yield the bis-sulfonamide (step c).

Scheme 4

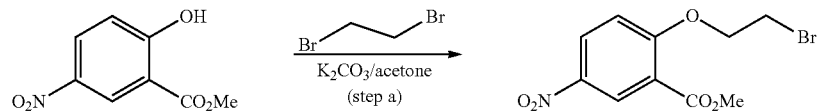

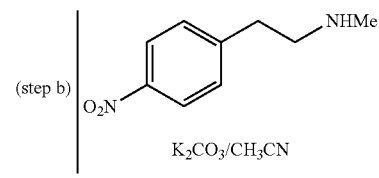

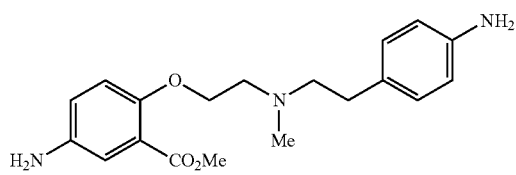
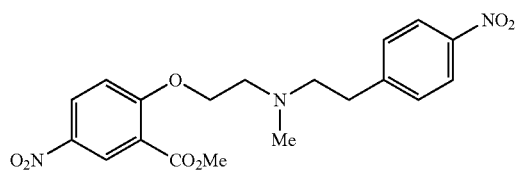

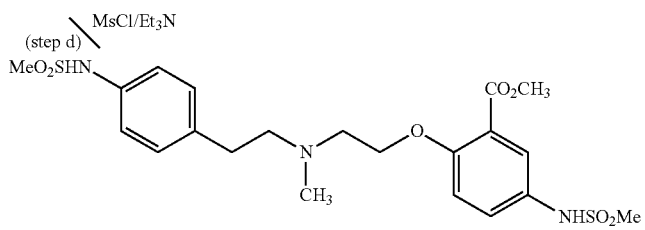

Scheme 4 shows the synthesis of various molecules containing an ester functionality directly attached to the phenoxy-portion of dofetilide. Commercially available 5-nitro salicylic acid can be alkylated with 1,2 dibromoethane in the presence of potassium carbonate in acetone to give the bromo-ester (step a). Treatment of the bromo-ester with N-methyl-4-nitrophenethyl amine in the presence of potassium carbonate in acetonitrile can afford the tertiary amine (step b). Subsequent reduction of the nitro groups using stannous chloride in methanol can provide the bis-anilino ester (step c). Reaction of the amino groups with methanesulfonyl chloride in methylene chloride in the presence of trimethylamine can afford the bis-sulfonamide (step d).

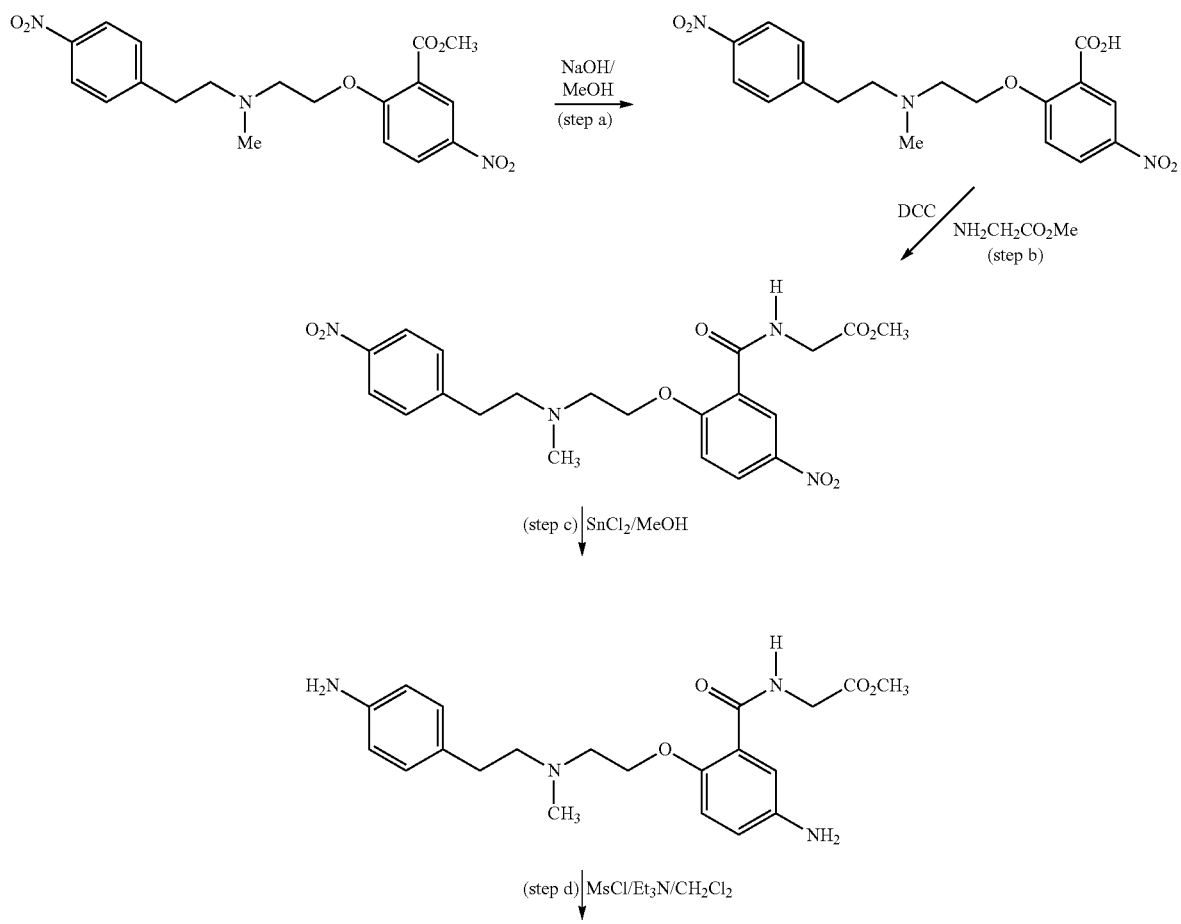

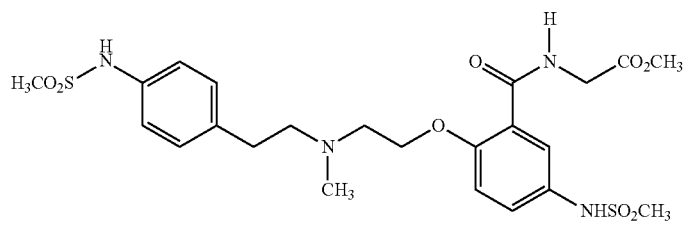

Scheme 5 shows the synthesis of analogs with the ester functionality attached to a pendant on the phenoxy portion of dofetilide. The previously described dinitro-ester Scheme 2 can be hydrolyzed to carboxylic acid (step a). Coupling of the ester with an amino acid ester such as glycine methyl ester using DCC in methylene chloride can provide the ester adduct (step b). Reduction of the nitro groups as previously described with stannous chloride can produce the bis-anilino ester (step c). Mesylation as previously described can afford the bis-sulfonamide (step d).

Scheme 6

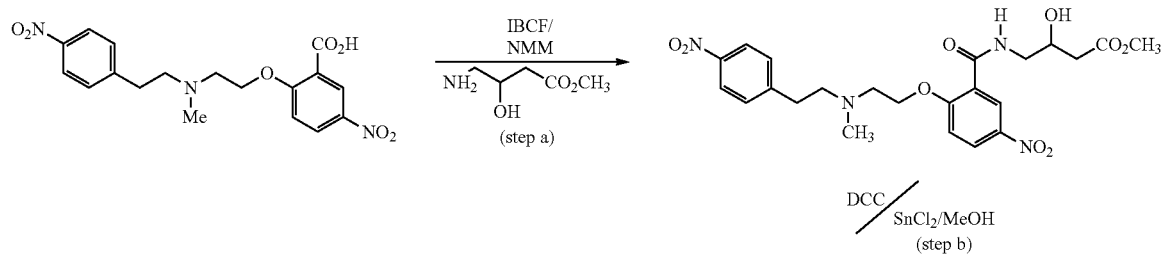

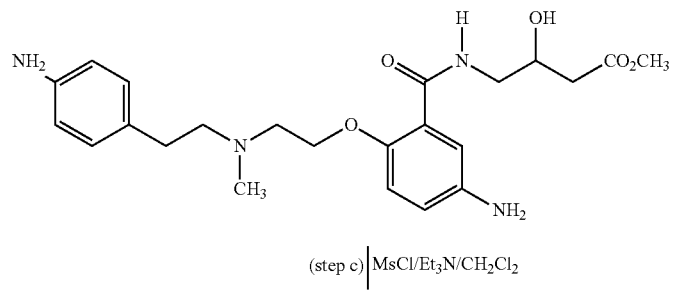

(step c) | MsCl/Et$_3$N/CH$_2$Cl$_2$

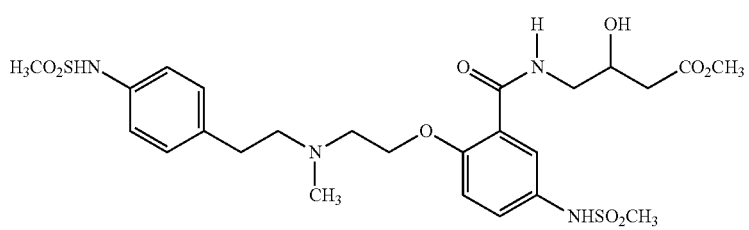

Scheme 6 shows the synthesis of analogs with the ester functionality attached to a pendant on the phenoxy portion of dofetilide. The previously described dinitro-carboxylic acid described in Scheme 3 can be coupled with 3-hydroxy-4-amino butyric acid methyl ester using IBCF in methylene chloride using and NMM to afford the hydroxy ester adduct (step a). Reduction of the nitro groups as previously described with stannous chloride can produce the bis-anilino ester (step b). Mesylation as previously described can afford the bis-sulfonamide (step c).

Scheme 7

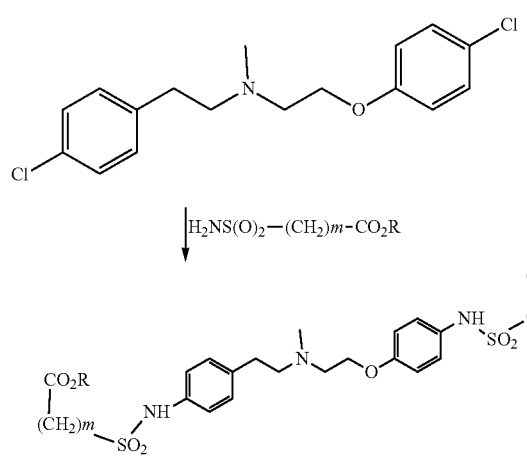

Scheme 7 shows a route for preparation of dofetilide analogs wherein both ends are capped (Formula 1). The known compound, 2-(4-chlorophenoxy)-N-[2-(4-chlorophenyl)ethyl]-N-methylethan-1-amine, can be reacted with an appropriately substituted sulfonamide to arrive at Formula 1.

Scheme 8

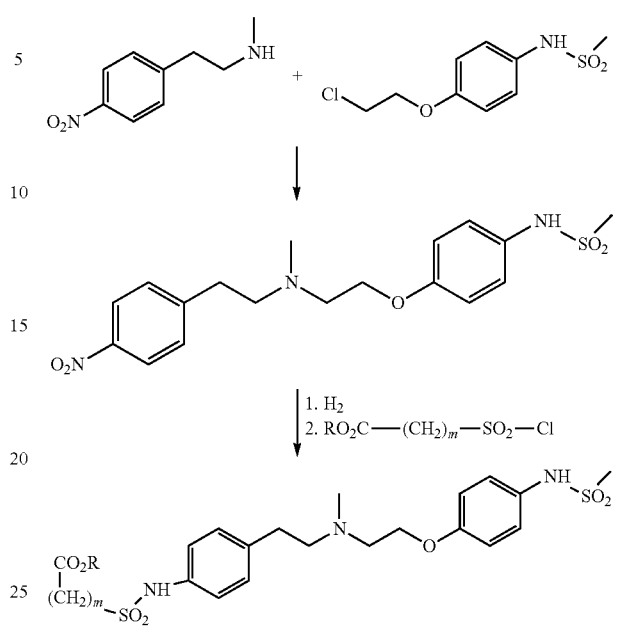

Scheme 8 shows a route for preparation of dofetilide analogs wherein the benzyl side has a capped sulfonamide (Formula 2), but not the phenoxy side. The starting 4-(2-chloroethoxy)-N-(methylsulfonyl)aniline is reacted with N-methyl-2-(4-nitrophenyl)ethan-1-amine to provide the nitro intermediate. The nitro moiety can then be hydrogenated and reacted with an appropriately substituted sulfonyl chloride to arrive at Formula 2.

Scheme 9

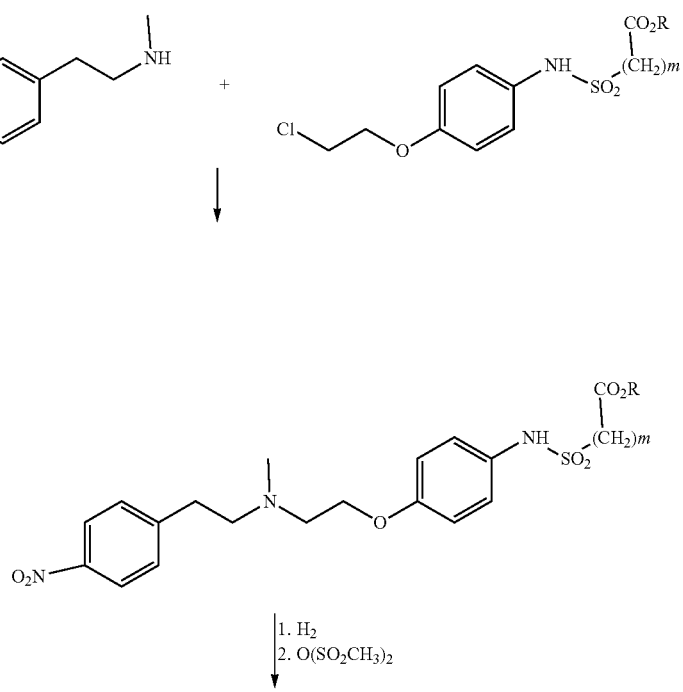

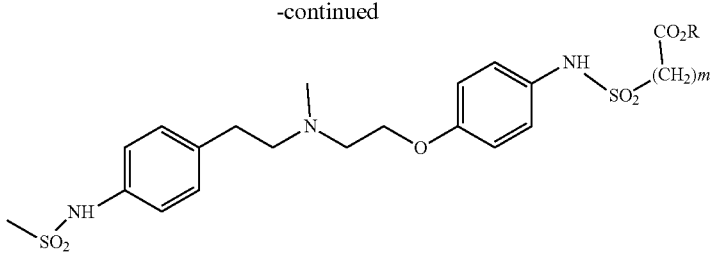

Scheme 9 shows a route for preparation of dofetilide analogs wherein the phenoxy side has a capped sulfonamide (Formula 3), but not the benzyl side. The starting 4-(2-chloroethoxy)-N—(RO$_2$(CH$_2$)$_m$-sulfonyl)aniline is reacted with N-methyl-2-(4-nitrophenyl)ethan-1-amine to provide the nitro intermediate. The nitro group can then be hydrogenated and reacted with methylsulfonic anhydride to arrive at Formula 3.

Other features of the aspects will become apparent in the course of the following descriptions of exemplary embodiments that are given for illustration of the aspects and are not intended to be limiting thereof.

EXAMPLES

The examples in the tables below can be prepared according to the methods of the scheme numbers provided for each example.

TABLE 1

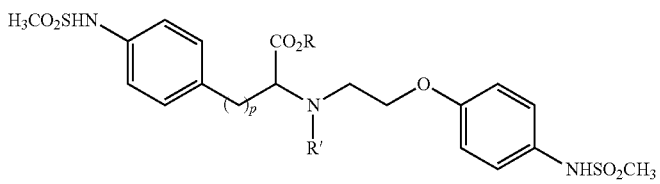

| Ex. # | R | n | R' | Synthesis Route |
|---|---|---|---|---|
| 1. | CH$_3$ | 1 | CH$_3$ | Scheme 1 |
| 2. | CH$_2$CH$_3$ | 1 | CH$_3$ | Scheme 1 |
| 3. | CH$_2$CH$_2$CH$_3$ | 1 | CH$_3$ | Scheme 1 |
| 4. | CH$_2$CH=CH$_2$ | 1 | CH$_3$ | Scheme 1 |
| 5. | CH$_3$ | 2 | CH$_3$ | Scheme 1 |
| 6. | CH$_2$CH$_3$ | 2 | CH$_3$ | Scheme 1 |
| 7. | CH$_2$CH$_2$CH$_3$ | 2 | CH$_3$ | Scheme 1 |
| 8. | CH$_2$CH=CH$_2$ | 2 | CH$_3$ | Scheme 1 |
| 9. | CH$_3$ | 1 | CH$_2$C$_6$H$_5$ | Scheme 1 |
| 10. | CH$_2$CH$_3$ | 1 | CH$_2$C$_6$H$_5$ | Scheme 1 |
| 11. | CH$_2$CH$_2$CH$_3$ | 1 | CH$_2$C$_6$H$_5$ | Scheme 1 |
| 12. | CH$_2$CH=CH$_2$ | 1 | CH$_2$C$_6$H$_5$ | Scheme 1 |
| 13. | CH$_3$ | 2 | CH$_2$C$_6$H$_5$ | Scheme 1 |
| 14. | CH$_2$CH$_3$ | 2 | CH$_2$C$_6$H$_5$ | Scheme 1 |
| 15. | CH$_2$CH$_2$CH$_3$ | 2 | CH$_2$C$_6$H$_5$ | Scheme 1 |
| 16. | CH$_2$CH=CH$_2$ | 2 | CH$_2$C$_6$H$_5$ | Scheme 1 |
| 17. | CH$_3$ | 1 | CH$_2$C$_6$H$_5$ | Scheme 1 |
| 18. | CH$_2$CH$_3$ | 1 | COCH$_3$ | Scheme 1 |
| 19. | CH$_2$CH$_2$CH$_3$ | 1 | COCH$_3$ | Scheme 1 |
| 20. | CH$_2$CH=CH$_2$ | 1 | COCH$_3$ | Scheme 1 |
| 21. | CH$_3$ | 2 | COCH$_3$ | Scheme 1 |
| 22. | CH$_2$CH$_3$ | 2 | COCH$_3$ | Scheme 1 |
| 23. | CH$_2$CH$_2$CH$_3$ | 2 | COCH$_3$ | Scheme 1 |
| 24. | CH$_2$CH=CH$_2$ | 2 | COCH$_3$ | Scheme 1 |

TABLE 2

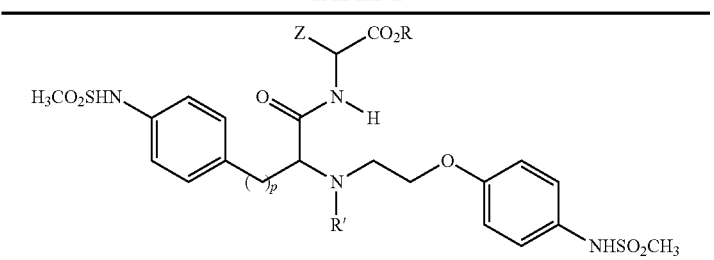

| Ex. # | R | n | Z | R' | Synthesis Route |
|---|---|---|---|---|---|
| 1. | CH$_3$ | 1 | H | CH$_3$ | Scheme 2 |
| 2. | CH$_2$CH$_3$ | 1 | H | CH$_3$ | Scheme 2 |
| 3. | CH$_2$CH$_2$CH$_3$ | 1 | H | CH$_3$ | Scheme 2 |
| 4. | CH$_2$CH=CH$_2$ | 1 | H | CH$_3$ | Scheme 2 |
| 5. | CH$_3$ | 1 | CH$_3$ | CH$_3$ | Scheme 2 |
| 6. | CH$_2$CH$_3$ | 1 | CH$_3$ | CH$_3$ | Scheme 2 |
| 7. | CH$_2$CH$_2$CH$_3$ | 1 | CH$_3$ | CH$_3$ | Scheme 2 |
| 8. | CH$_2$CH=CH$_2$ | 1 | CH$_3$ | CH$_3$ | Scheme 2 |
| 9. | CH$_3$ | 1 | CH$_2$OH | CH$_3$ | Scheme 2 |
| 10. | CH$_2$CH$_3$ | 1 | CH$_2$OH | CH$_3$ | Scheme 2 |
| 11. | CH$_2$CH$_2$CH$_3$ | 1 | CH$_2$OH | CH$_3$ | Scheme 2 |
| 12. | CH$_2$CH=CH$_2$ | 1 | CH$_2$OH | CH$_3$ | Scheme 2 |
| 13. | CH$_3$ | 2 | H | CH$_3$ | Scheme 2 |
| 14. | CH$_2$CH$_3$ | 2 | H | CH$_3$ | Scheme 2 |
| 15. | CH$_2$CH$_2$CH$_3$ | 2 | H | CH$_3$ | Scheme 2 |
| 16. | CH$_2$CH=CH$_2$ | 2 | H | CH$_3$ | Scheme 2 |
| 17. | CH$_3$ | 2 | CH$_3$ | CH$_3$ | Scheme 2 |
| 18. | CH$_2$CH$_3$ | 2 | CH$_3$ | CH$_3$ | Scheme 2 |
| 19. | CH$_2$CH$_2$CH$_3$ | 2 | CH$_3$ | CH$_3$ | Scheme 2 |
| 20. | CH$_2$CH=CH$_2$ | 2 | CH$_3$ | CH$_3$ | Scheme 2 |
| 21. | CH$_3$ | 2 | CH$_2$OH | CH$_3$ | Scheme 2 |
| 22. | CH$_2$CH$_3$ | 2 | CH$_2$OH | CH$_3$ | Scheme 2 |
| 23. | CH$_2$CH$_2$CH$_3$ | 2 | CH$_2$OH | CH$_3$ | Scheme 2 |
| 24. | CH$_2$CH=CH$_2$ | 2 | CH$_2$OH | CH$_3$ | Scheme 2 |
| 25. | CH$_3$ | 1 | H | CH$_2$C$_6$H$_5$ | Scheme 2 |
| 26. | CH$_2$CH$_3$ | 1 | H | CH$_2$C$_6$H$_5$ | Scheme 2 |
| 27. | CH$_2$CH$_2$CH$_3$ | 1 | H | CH$_2$C$_6$H$_5$ | Scheme 2 |
| 28. | CH$_2$CH=CH$_2$ | 1 | H | CH$_2$C$_6$H$_5$ | Scheme 2 |
| 29. | CH$_3$ | 1 | CH$_3$ | CH$_2$C$_6$H$_5$ | Scheme 2 |
| 30. | CH$_2$CH$_3$ | 1 | CH$_3$ | CH$_2$C$_6$H$_5$ | Scheme 2 |
| 31. | CH$_2$CH$_2$CH$_3$ | 1 | CH$_3$ | CH$_2$C$_6$H$_5$ | Scheme 2 |
| 32. | CH$_2$CH=CH$_2$ | 1 | CH$_3$ | CH$_2$C$_6$H$_5$ | Scheme 2 |
| 33. | CH$_3$ | 1 | CH$_2$OH | CH$_2$C$_6$H$_5$ | Scheme 2 |
| 34. | CH$_2$CH$_3$ | 1 | CH$_2$OH | CH$_2$C$_6$H$_5$ | Scheme 2 |
| 35. | CH$_2$CH$_2$CH$_3$ | 1 | CH$_2$OH | CH$_2$C$_6$H$_5$ | Scheme 2 |
| 36. | CH$_2$CH=CH$_2$ | 1 | CH$_2$OH | CH$_2$C$_6$H$_5$ | Scheme 2 |
| 37. | CH$_3$ | 2 | H | CH$_2$C$_6$H$_5$ | Scheme 2 |
| 38. | CH$_2$CH$_3$ | 2 | H | CH$_2$C$_6$H$_5$ | Scheme 2 |
| 39. | CH$_2$CH$_2$CH$_3$ | 2 | H | CH$_2$C$_6$H$_5$ | Scheme 2 |
| 40. | CH$_2$CH=CH$_2$ | 2 | H | CH$_2$C$_6$H$_5$ | Scheme 2 |
| 41. | CH$_3$ | 2 | CH$_3$ | CH$_2$C$_6$H$_5$ | Scheme 2 |
| 42. | CH$_2$CH$_3$ | 2 | CH$_3$ | CH$_2$C$_6$H$_5$ | Scheme 2 |
| 43. | CH$_2$CH$_2$CH$_3$ | 2 | CH$_3$ | CH$_2$C$_6$H$_5$ | Scheme 2 |
| 44. | CH$_2$CH=CH$_2$ | 2 | CH$_3$ | CH$_2$C$_6$H$_5$ | Scheme 2 |
| 45. | CH$_3$ | 2 | CH$_2$OH | CH$_2$C$_6$H$_5$ | Scheme 2 |
| 46. | CH$_2$CH$_3$ | 2 | CH$_2$OH | CH$_2$C$_6$H$_5$ | Scheme 2 |
| 47. | CH$_2$CH$_2$CH$_3$ | 2 | CH$_2$OH | CH$_2$C$_6$H$_5$ | Scheme 2 |
| 48. | CH$_2$CH=CH$_2$ | 2 | CH$_2$OH | CH$_2$C$_6$H$_5$ | Scheme 2 |
| 49. | CH$_3$ | 1 | H | COCH$_3$ | Scheme 2 |
| 50. | CH$_2$CH$_3$ | 1 | H | COCH$_3$ | Scheme 2 |
| 51. | CH$_2$CH$_2$CH$_3$ | 1 | H | COCH$_3$ | Scheme 2 |
| 52. | CH$_2$CH=CH$_2$ | 1 | H | COCH$_3$ | Scheme 2 |
| 53. | CH$_3$ | 1 | CH$_3$ | COCH$_3$ | Scheme 2 |
| 54. | CH$_2$CH$_3$ | 1 | CH$_3$ | COCH$_3$ | Scheme 2 |
| 55. | CH$_2$CH$_2$CH$_3$ | 1 | CH$_3$ | COCH$_3$ | Scheme 2 |
| 56. | CH$_2$CH=CH$_2$ | 1 | CH$_3$ | COCH$_3$ | Scheme 2 |
| 57. | CH$_3$ | 1 | CH$_2$OH | COCH$_3$ | Scheme 2 |
| 58. | CH$_2$CH$_3$ | 1 | CH$_2$OH | COCH$_3$ | Scheme 2 |
| 59. | CH$_2$CH$_2$CH$_3$ | 1 | CH$_2$OH | COCH$_3$ | Scheme 2 |
| 60. | CH$_2$CH=CH$_2$ | 1 | CH$_2$OH | COCH$_3$ | Scheme 2 |
| 61. | CH$_3$ | 2 | H | COCH$_3$ | Scheme 2 |
| 62. | CH$_2$CH$_3$ | 2 | H | COCH$_3$ | Scheme 2 |
| 63. | CH$_2$CH$_2$CH$_3$ | 2 | H | COCH$_3$ | Scheme 2 |
| 64. | CH$_2$CH=CH$_2$ | 2 | H | COCH$_3$ | Scheme 2 |
| 65. | CH$_3$ | 2 | CH$_3$ | COCH$_3$ | Scheme 2 |
| 66. | CH$_2$CH$_3$ | 2 | CH$_3$ | COCH$_3$ | Scheme 2 |

TABLE 2-continued

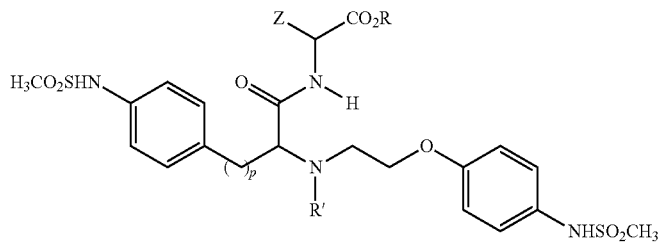

| Ex. # | R | n | Z | R' | Synthesis Route |
|---|---|---|---|---|---|
| 67. | CH$_2$CH$_2$CH$_3$ | 2 | CH$_3$ | COCH$_3$ | Scheme 2 |
| 68. | CH$_2$CH=CH$_2$ | 2 | CH$_3$ | COCH$_3$ | Scheme 2 |
| 69. | CH$_3$ | 2 | CH$_2$OH | COCH$_3$ | Scheme 2 |
| 70. | CH$_2$CH$_3$ | 2 | CH$_2$OH | COCH$_3$ | Scheme 2 |
| 71. | CH$_2$CH$_2$CH$_3$ | 2 | CH$_2$OH | COCH$_3$ | Scheme 2 |
| 72. | CH$_2$CH=CH$_2$ | 2 | CH$_2$OH | COCH$_3$ | Scheme 2 |

TABLE 3

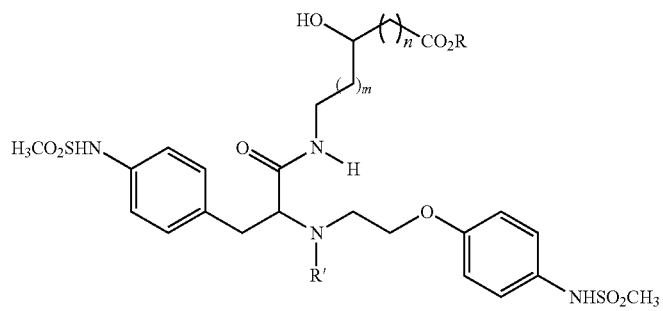

| Ex. # | R | m | n | R' | Synthesis Route |
|---|---|---|---|---|---|
| 1. | CH$_3$ | 1 | 0 | CH$_3$ | Scheme 3 |
| 2. | CH$_2$CH$_3$ | 1 | 0 | CH$_3$ | Scheme 3 |
| 3. | CH$_2$CH$_2$CH$_3$ | 1 | 0 | CH$_3$ | Scheme 3 |
| 4. | CH$_2$CH=CH$_2$ | 1 | 0 | CH$_3$ | Scheme 3 |
| 5. | CH$_3$ | 0 | 1 | CH$_3$ | Scheme 3 |
| 6. | CH$_2$CH$_3$ | 0 | 1 | CH$_3$ | Scheme 3 |
| 7. | CH$_2$CH$_2$CH$_3$ | 0 | 1 | CH$_3$ | Scheme 3 |
| 8. | CH$_2$CH=CH$_2$ | 0 | 1 | CH$_3$ | Scheme 3 |
| 9. | CH$_3$ | 1 | 0 | COCH$_3$ | Scheme 3 |
| 10. | CH$_2$CH$_3$ | 1 | 0 | COCH$_3$ | Scheme 3 |
| 11. | CH$_2$CH$_2$CH$_3$ | 1 | 0 | COCH$_3$ | Scheme 3 |
| 12. | CH$_2$CH=CH$_2$ | 1 | 0 | COCH$_3$ | Scheme 3 |
| 13. | CH$_3$ | 0 | 1 | COCH$_3$ | Scheme 3 |
| 14. | CH$_2$CH$_3$ | 0 | 1 | COCH$_3$ | Scheme 3 |
| 15. | CH$_2$CH$_2$CH$_3$ | 0 | 1 | COCH$_3$ | Scheme 3 |
| 16. | CH$_2$CH=CH$_2$ | 0 | 1 | COCH$_3$ | Scheme 3 |

TABLE 4A

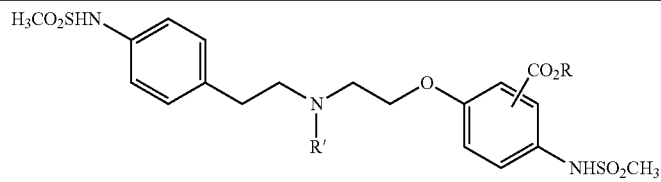

| Ex. # | R | R' | Synthesis Route |
|---|---|---|---|
| 1. | $CH_3$ | $CH_3$ | Scheme 4 |
| 2. | $CH_2CH_3$ | $CH_3$ | Scheme 4 |
| 3. | $CH_2CH_2CH_3$ | $CH_3$ | Scheme 4 |
| 4. | $CH_2CH=CH_2$ | $CH_3$ | Scheme 4 |
| 5. | $CH_3$ | $CH_2C_6H_5$ | Scheme 4 |
| 6. | $CH_2CH_3$ | $CH_2C_6H_5$ | Scheme 4 |
| 7. | $CH_2CH_2CH_3$ | $CH_2C_6H_5$ | Scheme 4 |
| 8. | $CH_2CH=CH_2$ | $CH_2C_6H_5$ | Scheme 4 |
| 9. | $CH_3$ | $COCH_3$ | Scheme 4 |
| 10. | $CH_2CH_3$ | $COCH_3$ | Scheme 4 |
| 11. | $CH_2CH_2CH_3$ | $COCH_3$ | Scheme 4 |
| 12. | $CH_2CH=CH_2$ | $COCH_3$ | Scheme 4 |
| 13. | $CH_3$ | $CH_3$ | Scheme 4 |
| 14. | $CH_2CH_3$ | $CH_3$ | Scheme 4 |
| 15. | $CH_2CH_2CH_3$ | $CH_3$ | Scheme 4 |
| 16. | $CH_2CH=CH_2$ | $CH_3$ | Scheme 4 |
| 17. | $CH_3$ | $CH_2C_6H_5$ | Scheme 4 |
| 18. | $CH_2CH_3$ | $CH_2C_6H_5$ | Scheme 4 |
| 19. | $CH_2CH_2CH_3$ | $CH_2C_6H_5$ | Scheme 4 |
| 20. | $CH_2CH=CH_2$ | $CH_2C_6H_5$ | Scheme 4 |
| 21. | $CH_3$ | $COCH_3$ | Scheme 4 |
| 22. | $CH_2CH_3$ | $COCH_3$ | Scheme 4 |
| 23. | $CH_2CH_2CH_3$ | $COCH_3$ | Scheme 4 |
| 24. | $CH_2CH=CH_2$ | $COCH_3$ | Scheme 4 |

TABLE 4B

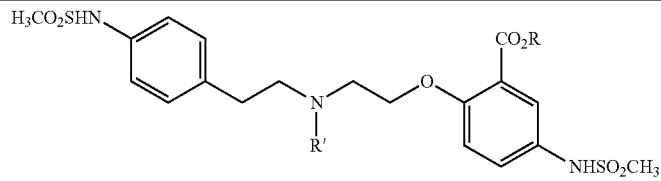

| Ex. # | R | R' | Synthesis Route |
|---|---|---|---|
| 1. | $CH_3$ | $CH_3$ | Scheme 4 |
| 2. | $CH_2CH_3$ | $CH_3$ | Scheme 4 |
| 3. | $CH_2CH_2CH_3$ | $CH_3$ | Scheme 4 |
| 4. | $CH_2CH=CH_2$ | $CH_3$ | Scheme 4 |
| 5. | $CH_3$ | $CH_2C_6H_5$ | Scheme 4 |
| 6. | $CH_2CH_3$ | $CH_2C_6H_5$ | Scheme 4 |
| 7. | $CH_2CH_2CH_3$ | $CH_2C_6H_5$ | Scheme 4 |
| 8. | $CH_2CH=CH_2$ | $CH_2C_6H_5$ | Scheme 4 |
| 9. | $CH_3$ | $COCH_3$ | Scheme 4 |
| 10. | $CH_2CH_3$ | $COCH_3$ | Scheme 4 |
| 11. | $CH_2CH_2CH_3$ | $COCH_3$ | Scheme 4 |
| 12. | $CH_2CH=CH_2$ | $COCH_3$ | Scheme 4 |
| 13. | $CH_3$ | $CH_3$ | Scheme 4 |
| 14. | $CH_2CH_3$ | $CH_3$ | Scheme 4 |
| 15. | $CH_2CH_2CH_3$ | $CH_3$ | Scheme 4 |
| 16. | $CH_2CH=CH_2$ | $CH_3$ | Scheme 4 |
| 17. | $CH_3$ | $CH_2C_6H_5$ | Scheme 4 |
| 18. | $CH_2CH_3$ | $CH_2C_6H_5$ | Scheme 4 |
| 19. | $CH_2CH_2CH_3$ | $CH_2C_6H_5$ | Scheme 4 |
| 20. | $CH_2CH=CH_2$ | $CH_2C_6H_5$ | Scheme 4 |
| 21. | $CH_3$ | $COCH_3$ | Scheme 4 |
| 22. | $CH_2CH_3$ | $COCH_3$ | Scheme 4 |
| 23. | $CH_2CH_2CH_3$ | $COCH_3$ | Scheme 4 |
| 24. | $CH_2CH=CH_2$ | $COCH_3$ | Scheme 4 |

TABLE 5A

Structure: H₃CO₂SHN-C₆H₄-CH₂CH₂-N(R')-CH₂CH₂-O-[benzene with C(=O)NH-CH(Z)-CO₂R and NHSO₂CH₃]

| Ex. # | R | Z | R' | Synthesis Route |
|---|---|---|---|---|
| 1. | CH₃ | H | CH₃ | Scheme 5 |
| 2. | CH₂CH₃ | H | CH₃ | Scheme 5 |
| 3. | CH₂CH₂CH₃ | H | CH₃ | Scheme 5 |
| 4. | CH₂CH=CH₂ | H | CH₃ | Scheme 5 |
| 5. | CH₃ | CH₃ | CH₃ | Scheme 5 |
| 6. | CH₂CH₃ | CH₃ | CH₃ | Scheme 5 |
| 7. | CH₂CH₂CH₃ | CH₃ | CH₃ | Scheme 5 |
| 8. | CH₂CH=CH₂ | CH₃ | CH₃ | Scheme 5 |
| 9. | CH₃ | CH₂OH | CH₃ | Scheme 5 |
| 10. | CH₂CH₃ | CH₂OH | CH₃ | Scheme 5 |
| 11. | CH₂CH₂CH₃ | CH₂OH | CH₃ | Scheme 5 |
| 12. | CH₂CH=CH₂ | CH₂OH | CH₃ | Scheme 5 |
| 13. | CH₃ | H | CH₂C₆H₅ | Scheme 5 |
| 14. | CH₂CH₃ | H | CH₂C₆H₅ | Scheme 5 |
| 15. | CH₂CH₂CH₃ | H | CH₂C₆H₅ | Scheme 5 |
| 16. | CH₂CH=CH₂ | H | CH₂C₆H₅ | Scheme 5 |
| 17. | CH₃ | CH₃ | CH₂C₆H₅ | Scheme 5 |
| 18. | CH₂CH₃ | CH₃ | CH₂C₆H₅ | Scheme 5 |
| 19. | CH₂CH₂CH₃ | CH₃ | CH₂C₆H₅ | Scheme 5 |
| 20. | CH₂CH=CH₂ | CH₃ | CH₂C₆H₅ | Scheme 5 |
| 21. | CH₃ | CH₂OH | CH₂C₆H₅ | Scheme 5 |
| 22. | CH₂CH₃ | CH₂OH | CH₂C₆H₅ | Scheme 5 |
| 23. | CH₂CH₂CH₃ | CH₂OH | CH₂C₆H₅ | Scheme 5 |
| 24. | CH₂CH=CH₂ | CH₂OH | CH₂C₆H₅ | Scheme 5 |
| 25. | CH₃ | H | COCH₃ | Scheme 5 |
| 26. | CH₂CH₃ | H | COCH₃ | Scheme 5 |
| 27. | CH₂CH₂CH₃ | H | COCH₃ | Scheme 5 |
| 28. | CH₂CH=CH₂ | H | COCH₃ | Scheme 5 |
| 29. | CH₃ | CH₃ | COCH₃ | Scheme 5 |
| 30. | CH₂CH₃ | CH₃ | COCH₃ | Scheme 5 |
| 31. | CH₂CH₂CH₃ | CH₃ | COCH₃ | Scheme 5 |
| 32. | CH₂CH=CH₂ | CH₃ | COCH₃ | Scheme 5 |
| 33. | CH₃ | CH₂OH | COCH₃ | Scheme 5 |
| 34. | CH₂CH₃ | CH₂OH | COCH₃ | Scheme 5 |
| 35. | CH₂CH₂CH₃ | CH₂OH | COCH₃ | Scheme 5 |
| 36. | CH₂CH=CH₂ | CH₂OH | COCH₃ | Scheme 5 |

TABLE 5B

Structure: H₃CO₂SHN-C₆H₄-CH₂CH₂-N(R')-CH₂CH₂-O-[benzene with C(=O)NH-CH(Z)-CO₂R and NHSO₂CH₃]

| Ex. # | R | Z | R' | Synthesis Route |
|---|---|---|---|---|
| 1. | CH₃ | H | CH₃ | Scheme 5 |
| 2. | CH₂CH₃ | H | CH₃ | Scheme 5 |
| 3. | CH₂CH₂CH₃ | H | CH₃ | Scheme 5 |
| 4. | CH₂CH=CH₂ | H | CH₃ | Scheme 5 |
| 5. | CH₃ | CH₃ | CH₃ | Scheme 5 |
| 6. | CH₂CH₃ | CH₃ | CH₃ | Scheme 5 |
| 7. | CH₂CH₂CH₃ | CH₃ | CH₃ | Scheme 5 |
| 8. | CH₂CH=CH₂ | CH₃ | CH₃ | Scheme 5 |
| 9. | CH₃ | CH₂OH | CH₃ | Scheme 5 |
| 10. | CH₂CH₃ | CH₂OH | CH₃ | Scheme 5 |
| 11. | CH₂CH₂CH₃ | CH₂OH | CH₃ | Scheme 5 |
| 12. | CH₂CH=CH₂ | CH₂OH | CH₃ | Scheme 5 |
| 13. | CH₃ | H | CH₂C₆H₅ | Scheme 5 |
| 14. | CH₂CH₃ | H | CH₂C₆H₅ | Scheme 5 |

TABLE 5B-continued

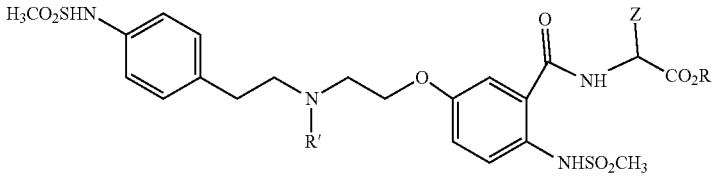

| Ex. # | R | Z | R' | Synthesis Route |
|---|---|---|---|---|
| 15. | $CH_2CH_2CH_3$ | H | $CH_2C_6H_5$ | Scheme 5 |
| 16. | $CH_2CH=CH_2$ | H | $CH_2C_6H_5$ | Scheme 5 |
| 17. | $CH_3$ | $CH_3$ | $CH_2C_6H_5$ | Scheme 5 |
| 18. | $CH_2CH_3$ | $CH_3$ | $CH_2C_6H_5$ | Scheme 5 |
| 19. | $CH_2CH_2CH_3$ | $CH_3$ | $CH_2C_6H_5$ | Scheme 5 |
| 20. | $CH_2CH=CH_2$ | $CH_3$ | $CH_2C_6H_5$ | Scheme 5 |
| 21. | $CH_3$ | $CH_2OH$ | $CH_2C_6H_5$ | Scheme 5 |
| 22. | $CH_2CH_3$ | $CH_2OH$ | $CH_2C_6H_5$ | Scheme 5 |
| 23. | $CH_2CH_2CH_3$ | $CH_2OH$ | $CH_2C_6H_5$ | Scheme 5 |
| 24. | $CH_2CH=CH_2$ | $CH_2OH$ | $CH_2C_6H_5$ | Scheme 5 |
| 25. | $CH_3$ | H | $COCH_3$ | Scheme 5 |
| 26. | $CH_2CH_3$ | H | $COCH_3$ | Scheme 5 |
| 27. | $CH_2CH_2CH_3$ | H | $COCH_3$ | Scheme 5 |
| 28. | $CH_2CH=CH_2$ | H | $COCH_3$ | Scheme 5 |
| 29. | $CH_3$ | $CH_3$ | $COCH_3$ | Scheme 5 |
| 30. | $CH_2CH_3$ | $CH_3$ | $COCH_3$ | Scheme 5 |
| 31. | $CH_2CH_2CH_3$ | $CH_3$ | $COCH_3$ | Scheme 5 |
| 32. | $CH_2CH=CH_2$ | $CH_3$ | $COCH_3$ | Scheme 5 |
| 33. | $CH_3$ | $CH_2OH$ | $COCH_3$ | Scheme 5 |
| 34. | $CH_2CH_3$ | $CH_2OH$ | $COCH_3$ | Scheme 5 |
| 35. | $CH_2CH_2CH_3$ | $CH_2OH$ | $COCH_3$ | Scheme 5 |
| 36. | $CH_2CH=CH_2$ | $CH_2OH$ | $COCH_3$ | Scheme 5 |

TABLE 6A

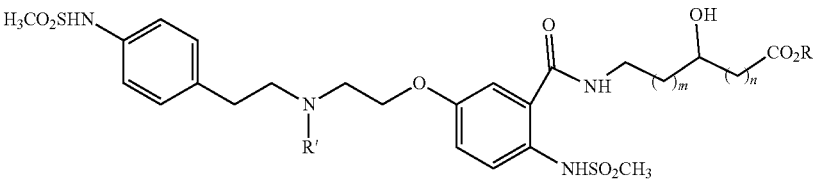

| Ex. # | R | m | n | R' | Synthesis Route |
|---|---|---|---|---|---|
| 1. | $CH_3$ | 1 | 0 | $CH_3$ | Scheme 6 |
| 2. | $CH_2CH_3$ | 1 | 0 | $CH_3$ | Scheme 6 |
| 3. | $CH_2CH_2CH_3$ | 1 | 0 | $CH_3$ | Scheme 6 |
| 4. | $CH_2CH=CH_2$ | 1 | 0 | $CH_3$ | Scheme 6 |
| 5. | $CH_3$ | 0 | 1 | $CH_3$ | Scheme 6 |
| 6. | $CH_2CH_3$ | 0 | 1 | $CH_3$ | Scheme 6 |
| 7. | $CH_2CH_2CH_3$ | 0 | 1 | $CH_3$ | Scheme 6 |
| 8. | $CH_2CH=CH_2$ | 0 | 1 | $CH_3$ | Scheme 6 |
| 9. | $CH_3$ | 1 | 0 | $COCH_3$ | Scheme 6 |
| 10. | $CH_2CH_3$ | 1 | 0 | $COCH_3$ | Scheme 6 |
| 11. | $CH_2CH_2CH_3$ | 1 | 0 | $COCH_3$ | Scheme 6 |
| 12. | $CH_2CH=CH_2$ | 1 | 0 | $COCH_3$ | Scheme 6 |
| 13. | $CH_3$ | 0 | 1 | $COCH_3$ | Scheme 6 |
| 14. | $CH_2CH_3$ | 0 | 1 | $COCH_3$ | Scheme 6 |
| 15. | $CH_2CH_2CH_3$ | 0 | 1 | $COCH_3$ | Scheme 6 |
| 16. | $CH_2CH=CH_2$ | 0 | 1 | $COCH_3$ | Scheme 6 |

TABLE 6B

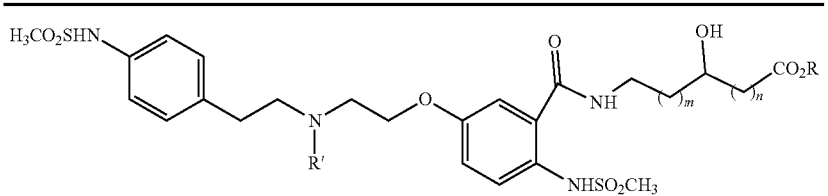

| Ex. # | R | m | n | R' | Synthesis Route |
| --- | --- | --- | --- | --- | --- |
| 1. | CH₃ | 1 | 0 | CH₃ | Scheme 6 |
| 2. | CH₂CH₃ | 1 | 0 | CH₃ | Scheme 6 |
| 3. | CH₂CH₂CH₃ | 1 | 0 | CH₃ | Scheme 6 |
| 4. | CH₂CH=CH₂ | 1 | 0 | CH₃ | Scheme 6 |
| 5. | CH₃ | 0 | 1 | CH₃ | Scheme 6 |
| 6. | CH₂CH₃ | 0 | 1 | CH₃ | Scheme 6 |
| 7. | CH₂CH₂CH₃ | 0 | 1 | CH₃ | Scheme 6 |
| 8. | CH₂CH=CH₂ | 0 | 1 | CH₃ | Scheme 6 |
| 9. | CH₃ | 1 | 0 | COCH₃ | Scheme 6 |
| 10. | CH₂CH₃ | 1 | 0 | COCH₃ | Scheme 6 |
| 11. | CH₂CH₂CH₃ | 1 | 0 | COCH₃ | Scheme 6 |
| 12. | CH₂CH=CH₂ | 1 | 0 | COCH₃ | Scheme 6 |
| 13. | CH₃ | 0 | 1 | COCH₃ | Scheme 6 |
| 14. | CH₂CH₃ | 0 | 1 | COCH₃ | Scheme 6 |
| 15. | CH₂CH₂CH₃ | 0 | 1 | COCH₃ | Scheme 6 |
| 16. | CH₂CH=CH₂ | 0 | 1 | COCH₃ | Scheme 6 |

TABLE 7

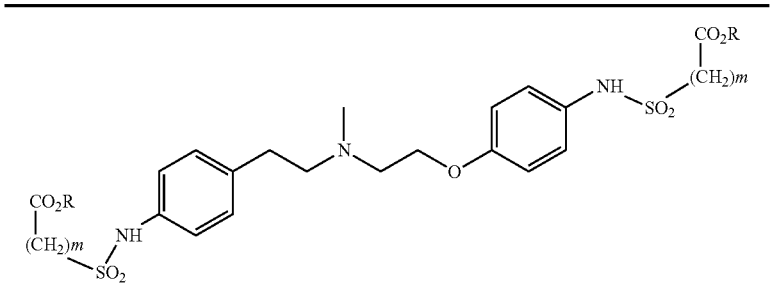

| Ex. # | R | m | Synthesis Route |
| --- | --- | --- | --- |
| 1. | CH₃ | 0 | Scheme 7 |
| 2. | CH₂CH₃ | 0 | Scheme 7 |
| 3. | CH₂CH₂CH₃ | 0 | Scheme 7 |
| 4. | CH₂CH=CH₂ | 0 | Scheme 7 |
| 5. | CH₃ | 1 | Scheme 7 |
| 6. | CH₂CH₃ | 1 | Scheme 7 |
| 7. | CH₂CH₂CH₃ | 1 | Scheme 7 |
| 8. | CH₂CH=CH₂ | 1 | Scheme 7 |
| 9. | CH₃ | 2 | Scheme 7 |
| 10. | CH₂CH₃ | 2 | Scheme 7 |
| 11. | CH₂CH₂CH₃ | 2 | Scheme 7 |
| 12. | CH₂CH=CH₂ | 2 | Scheme 7 |

TABLE 8

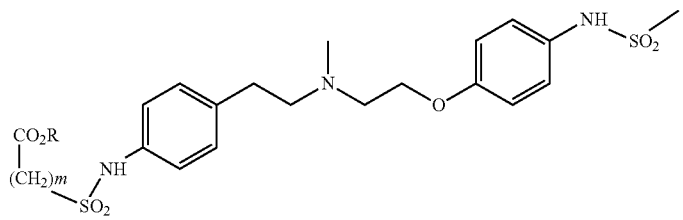

| Ex.# | R | m | Synthesis Route |
| --- | --- | --- | --- |
| 1. | $CH_3$ | 0 | Scheme 8 |
| 2. | $CH_2CH_3$ | 0 | Scheme 8 |
| 3. | $CH_2CH_2CH_3$ | 0 | Scheme 8 |
| 4. | $CH_2CH=CH_2$ | 0 | Scheme 8 |
| 5. | $CH_3$ | 1 | Scheme 8 |
| 6. | $CH_2CH_3$ | 1 | Scheme 8 |
| 7. | $CH_2CH_2CH_3$ | 1 | Scheme 8 |
| 8. | $CH_2CH=CH_2$ | 1 | Scheme 8 |
| 9. | $CH_3$ | 2 | Scheme 8 |
| 10. | $CH_2CH_3$ | 2 | Scheme 8 |
| 11. | $CH_2CH_2CH_3$ | 2 | Scheme 8 |
| 12. | $CH_2CH=CH_2$ | 2 | Scheme 8 |

TABLE 9

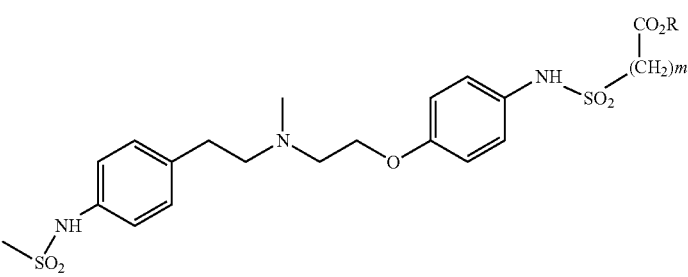

| Ex. # | R | m | Synthesis Route |
| --- | --- | --- | --- |
| 1. | $CH_3$ | 0 | Scheme 9 |
| 2. | $CH_2CH_3$ | 0 | Scheme 9 |
| 3. | $CH_2CH_2CH_3$ | 0 | Scheme 9 |
| 4. | $CH_2CH=CH_2$ | 0 | Scheme 9 |
| 5. | $CH_3$ | 1 | Scheme 9 |
| 6. | $CH_2CH_3$ | 1 | Scheme 9 |
| 7. | $CH_2CH_2CH_3$ | 1 | Scheme 9 |
| 8. | $CH_2CH=CH_2$ | 1 | Scheme 9 |
| 9. | $CH_3$ | 2 | Scheme 9 |
| 10. | $CH_2CH_3$ | 2 | Scheme 9 |
| 11. | $CH_2CH_2CH_3$ | 2 | Scheme 9 |
| 12. | $CH_2CH=CH_2$ | 2 | Scheme 9 |

Numerous modifications and variations of the aspects described herein are possible in light of the above teachings. It is therefore to be understood that within the scope of the appended claims, the aspects may be practiced otherwise than as specifically described herein.

What is claimed is:

1. A compound of Formula I-III or a stereoisomer thereof:

Formula I

Formula II

Formula III wherein:
R is selected from H, $C_{1-6}$ alkyl, $C_{3-6}$ alkenyl, and $C_{3-6}$ alkynyl; and,
m is selected from 0 and 1;
or a pharmaceutically acceptable salt thereof.

2. A compound of claim 1, wherein the compound is of Formula I:

I wherein the compound is selected from the following table:

| | R | m |
|---|---|---|
| 1. | $CH_3$ | 0 |
| 2. | $CH_2CH_3$ | 0 |
| 3. | $CH_2CH_2CH_3$ | 0 |
| 4. | $CH_2CH=CH_2$ | 0 |
| 5. | $CH_3$ | 1 |
| 6. | $CH_2CH_3$ | 1 |
| 7. | $CH_2CH_2CH_3$ | 1 |
| 8. | $CH_2CH=CH_2$ | 1 |
| 9. | $CH_3$ | 2 |
| 10. | $CH_2CH_3$ | 2 |
| 11. | $CH_2CH_2CH_3$ | 2 |
| 12. | $CH_2CH=CH_2$ | 2 | or pharmaceutically acceptable salt thereof.

3. A compound of claim 1, wherein the compound is of Formula II:

II

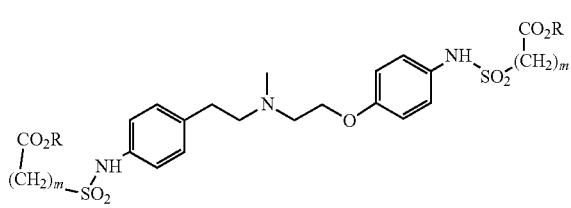

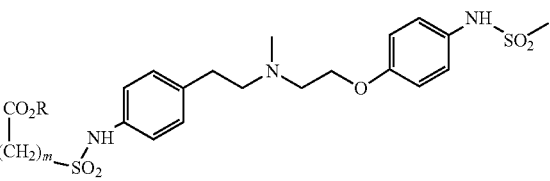

wherein the compound is selected from the following table:

|   | R | M |
|---|---|---|
| 1. | CH₃ | 0 |
| 2. | CH₂CH₃ | 0 |
| 3. | CH₂CH₂CH₃ | 0 |
| 4. | CH₂CH=CH₂ | 0 |
| 5. | CH₃ | 1 |
| 6. | CH₂CH₃ | 1 |
| 7. | CH₂CH₂CH₃ | 1 |
| 8. | CH₂CH=CH₂ | 1 |
| 9. | CH₃ | 2 |
| 10. | CH₂CH₃ | 2 |
| 11. | CH₂CH₂CH₃ | 2 |
| 12. | CH₂CH=CH₂ | 2 | or pharmaceutically acceptable salt thereof.

4. A compound of claim 1, wherein the compound is of Formula III:

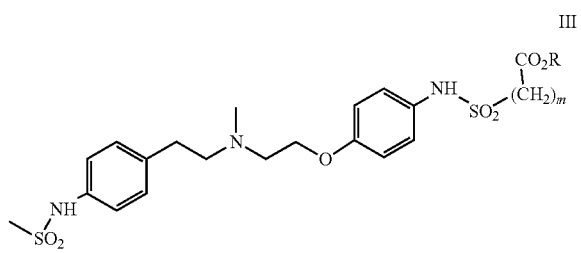

III wherein the compound is selected from the following table:

|   | R | m |
|---|---|---|
| 1. | CH₃ | 0 |
| 2. | CH₂CH₃ | 0 |
| 3. | CH₂CH₂CH₃ | 0 |
| 4. | CH₂CH=CH₂ | 0 |
| 5. | CH₃ | 1 |
| 6. | CH₂CH₃ | 1 |
| 7. | CH₂CH₂CH₃ | 1 |
| 8. | CH₂CH=CH₂ | 1 |
| 9. | CH₃ | 2 |
| 10. | CH₂CH₃ | 2 |
| 11. | CH₂CH₂CH₃ | 2 |
| 12. | CH₂CH=CH₂ | 2 | or pharmaceutically acceptable salt thereof.

5. A pharmaceutical composition, comprising: a therapeutically effective amount of a compound of claim 1 or pharmaceutically acceptable salt thereof and a pharmaceutically acceptable carrier.

6. A pharmaceutical composition, comprising: a therapeutically effective amount of a compound of claim 2 or pharmaceutically acceptable salt thereof and a pharmaceutically acceptable carrier.

7. A pharmaceutical composition, comprising: a therapeutically effective amount of a compound of claim 3 or pharmaceutically acceptable salt thereof and a pharmaceutically acceptable carrier.

8. A pharmaceutical composition, comprising: a therapeutically effective amount of a compound of claim 4 or pharmaceutically acceptable salt thereof and a pharmaceutically acceptable carrier.

9. A method of terminating or blocking the occurrence of an arrhythmia, comprising: administering to a patient in need thereof a therapeutically effective amount of a compound of claim 1 or pharmaceutically acceptable salt thereof, wherein the arrhythmia is selected from: paroxysmal atrial tachycardia, junctional ectopic tachycardia, atrial flutter, atrial fibrillation, atrial tachycardia, ventricular tachycardia, junctional tachycardia, and ventricular fibrillation.

10. A method of terminating or blocking the occurrence of an arrhythmia, comprising: administering to a patient in need thereof a therapeutically effective amount of a compound of claim 2 or pharmaceutically acceptable salt thereof, wherein the arrhythmia is selected from: paroxysmal atrial tachycardia, junctional ectopic tachycardia, atrial flutter, atrial fibrillation, atrial tachycardia, ventricular tachycardia, junctional tachycardia, and ventricular fibrillation.

11. A method of terminating or blocking the occurrence of an arrhythmia, comprising: administering to a patient in need thereof a therapeutically effective amount of a compound of claim 3 or pharmaceutically acceptable salt thereof, wherein the arrhythmia is selected from: paroxysmal atrial tachycardia, junctional ectopic tachycardia, atrial flutter, atrial fibrillation, atrial tachycardia, ventricular tachycardia, junctional tachycardia, and ventricular fibrillation.

12. A method of terminating or blocking the occurrence of an arrhythmia, comprising: administering to a patient in need thereof a therapeutically effective amount of a compound of claim 4 or pharmaceutically acceptable salt thereof, wherein the arrhythmia is selected from: paroxysmal atrial tachycardia, junctional ectopic tachycardia, atrial flutter, atrial fibrillation, atrial tachycardia, ventricular tachycardia, junctional tachycardia, and ventricular fibrillation.

* * * * *